US012734367B2

(12) United States Patent
Coult et al.

(10) Patent No.: US 12,734,367 B2
(45) Date of Patent: Sep. 15, 2026

(54) TECHNIQUES FOR PREDICTING AND TREATING REFRACTORY VENTRICULAR FIBRILLATION

(71) Applicant: University of Washington, Seattle, WA (US)

(72) Inventors: Jason Coult, Seattle, WA (US); Thomas Rea, Seattle, WA (US); Peter J. Kudenchuk, Seattle, WA (US); Heemun Kwok, Seattle, WA (US); Jose Nathan Kutz, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 19/126,999

(22) PCT Filed: Oct. 30, 2023

(86) PCT No.: PCT/US2023/036321
§ 371 (c)(1),
(2) Date: May 2, 2025

(87) PCT Pub. No.: WO2024/097141
PCT Pub. Date: May 10, 2024

(65) Prior Publication Data

US 2026/0000903 A1 Jan. 1, 2026

Related U.S. Application Data

(60) Provisional application No. 63/421,901, filed on Nov. 2, 2022.

(51) Int. Cl.
*A61N 1/39* (2006.01)
*G16H 50/70* (2018.01)

(52) U.S. Cl.
CPC ....... *A61N 1/3925* (2013.01); *A61N 1/39044* (2017.08); *G16H 50/70* (2018.01)

(58) Field of Classification Search
CPC ..... A61B 5/4848; A61B 5/7264; A61B 5/361; A61B 5/4836; A61B 5/726; A61B 5/349;
(Continued)

(56) References Cited

U.S. PATENT DOCUMENTS 7,171,269 B1 * 1/2007 Addison ................ A61B 5/361 600/509
10,448,853 B2 10/2019 Mahajan et al.
(Continued)

FOREIGN PATENT DOCUMENTS

KR 102448860 B1 10/2022

OTHER PUBLICATIONS

"Annual Report to the King County Council", https://www.kingcounty.gov/depts/health/emergency-medical-services/reports.aspx, Nov. 2019, 69 pages.
(Continued)

*Primary Examiner* — Carl H Layno
*Assistant Examiner* — Mary Grace Schlueter
(74) *Attorney, Agent, or Firm* — Katherine M. Mead; Lee & Hayes PC

(57) ABSTRACT

An example method includes identifying a first segment of an electrocardiogram (ECG) that ends prior to administration of an electrical shock and identifying at least one second segment of the ECG that begins after the administration of the electrical shock. The example method further includes predicting, based on the first segment and the at least one second segment, that the ECG is indicative of a defibrillation-resistant heart rhythm. The first segment is converted into a first scalogram, and the at least one segment is converted into at least one second scalogram. The defibril-
(Continued)

lation-resistant heart rhythm is predicted based on comparisons between the scalograms and the eigenscalograms. An indication of the predicted defibrillation-resistant heart rhythm is output.

20 Claims, 10 Drawing Sheets

(58) Field of Classification Search
CPC .. A61B 5/363; A61H 31/005; A61N 1/39044; A61N 1/3925; G16H 50/20; G16H 50/70
USPC ......... 607/5, 2; 600/508, 509, 510, 515, 518
See application file for complete search history.

(56) References Cited

U.S. PATENT DOCUMENTS

| | | | | |
|---|---|---|---|---|
| 10,548,499 | B2 | 2/2020 | Bayasi et al. | |
| 10,726,545 | B2 | 7/2020 | Marrouche et al. | |
| 2003/0153951 | A1 | 8/2003 | Ideker | |
| 2008/0109041 | A1 | 5/2008 | de Voir | |
| 2008/0269818 | A1* | 10/2008 | Sullivan | A61N 1/3925 607/10 |
| 2014/0207012 | A1 | 7/2014 | Coult et al. | |
| 2020/0305799 | A1 | 10/2020 | Cao et al. | |
| 2020/0316393 | A1* | 10/2020 | Chapman | A61N 1/3987 |
| 2022/0193431 | A1* | 6/2022 | Chapman | A61N 1/3925 |
| 2022/0369930 | A1 | 11/2022 | Robinson et al. | |

OTHER PUBLICATIONS

Aiello, et al., "Targeted Delivery of Electrical Shocks and Epinephrine, Guided by Ventricular Fibrillation Amplitude Spectral Area, Reduces Electrical and Adrenergic Myocardial Burden, Improving Survival in Swine", J Am Heart Assoc., vol. 10, No. 23, Dec. 2021, 11 pages.
Ajam, et al., "Reliability of the Cerebral Performance Category to classify neurological status among survivors of ventricular fibrillation arrest: a cohort study", Scand J Trauma Resusc Emerg Med., vol. 19, No. 38, Jun. 2011, 5 pages.
Attia, et al., "An artificial intelligence-enabled ECG algorithm for the identification of patients with atrial fibrillation during sinus rhythm: a retrospective analysis of outcome prediction", Lancet, vol. 394, No. 10201, Sep. 2019, pp. 861-867.
Bartos, et al., "Improved Survival With Extracorporeal Cardiopulmonary Resuscitation Despite Progressive Metabolic Derangement Associated With Prolonged Resuscitation", Circulation, vol. 141, No. 11, Mar. 2020, pp. 877-886.
Berdowski, et al., "Time in recurrent ventricular fibrillation and survival after out-of-hospital cardiac arrest", Circulation, vol. 122, No. 11, Sep. 2010, pp. 1101-1108.
Bhandari, et al., "Rhythm profiles and survival after out-of-hospital ventricular fibrillation cardiac arrest", Resuscitation, vol. 125, Apr. 2018, pp. 22-27.
Brown, et al., "Role of artificial intelligence in defibrillators: a narrative review", Open Heart, vol. 9, No. 2, Jul. 2022, 11 pages.
Brunton & Kutz, "Data-Driven Science and Engineering: Machine Learning, Dynamical Systems, and Control", 2nd ed. Cambridge University Press, 2022.
Chen, et al., "Decoding Artificial Intelligence to Achieve Diagnostic Excellence: Learning From Experts, Examples, and Experience", JAMA., vol. 328, No. 8, Aug. 2022, pp. 709-710.
Coult, et al., "A Machine Learning Algorithm To Predict Refractory Ventricular Fibrillation", American Heart Assoc., vol. 146, No. 1, Nov. 2022, 6 pages.
Coult, et al., "A method to predict ventricular fibrillation shock outcome during chest compressions", Comput Biol Med., vol. 129, No. 104136, Feb. 2021, 11 pages.
Coult, et al., "Continuous assessment of ventricular fibrillation prognostic status during CPR: Implications for resuscitation", Resuscitation, vol. 179, Oct. 2022, pp. 152-162.
Coult, et al., "Prediction of Shock-Refractory Ventricular Fibrillation During Resuscitation of Out-of-Hospital Cardiac Arrest", Circulation, vol. 148, No. 4, Jul. 2023, pp. 327-335.
Coult, et al., "Ventricular Fibrillation Waveform Analysis During Chest Compressions to Predict Survival From Cardiac Arrest", Circ Arrhythm Electrophysiol., vol. 12, No. 1, Jan. 2019, 20 pages.
Coult, et al., "Ventricular fibrillation waveform measures combined with prior shock outcome predict defibrillation success during cardiopulmonary resuscitation", J Electrocardiol., vol. 51, No. 1, Jan. 2018, pp. 99-106.
Cuocolo, et al., "Current applications of big data and machine learning in cardiology", J Geriatr Cardiol., vol. 16, No. 8, Aug. 2019, pp. 601-607.
De Graaf, et al., "Analyzing the heart rhythm during chest compressions: Performance and clinical value of a new AED algorithm", Resuscitation, vol. 162, May 2021, pp. 320-328.
Feeny, et al., "Machine Learning Prediction of Response to Cardiac Resynchronization Therapy: Improvement Versus Current Guidelines", Circ Arrhythm Electrophysiol., vol. 12, No. 7, Jul. 2019, 25 pages.
Gliner & White, "Electrocardiogram of defibrillation shocks delivered to out-of-hospital sudden cardiac arrest patients", Resuscitation, vol. 41, No. 2, Jul. 1999, pp. 133-144.
Holmen, et al., "Survival in ventricular fibrillation with emphasis on the number of defibrillations in relation to other factors at resuscitation", Resuscitation, vol. 113, Apr. 2017, pp. 33-38.
Hu, et al., "The performance of a new shock advisory algorithm to reduce interruptions during CPR", Resuscitation, vol. 143, Oct. 2019, pp. 1-9.
Karlis, et al., "Effects of early amiodarone administration during and immediately after cardiopulmonary resuscitation in a swine model", Acta Anaesthesiol Scand., vol. 58, No. 1, Jan. 2014, pp. 114-122.
Kwok, et al., "A method for continuous rhythm classification and early detection of ventricular fibrillation during CPR", Resuscitation, vol. 176, Jul. 2022, pp. 90-97.
Lautz, et al., "Hemodynamic-Directed Cardiopulmonary Resuscitation Improves Neurologic Outcomes and Mitochondrial Function in the Heart and Brain", Crit Care Med., vol. 47, No. 3, Mar. 2019, 16 pages.
Panchal, et al., "2018 American Heart Association Focused Update on Advanced Cardiovascular Life Support Use of Antiarrhythmic Drugs During and Immediately After Cardiac Arrest: An Update to the American Heart Association Guidelines for Cardiopulmonary Resuscitation and Emergency Cardiovascular Care", Circulation, vol. 138, No. 23, Dec. 2018, pp. 740-749.
Panchal, et al., "Part 3: Adult Basic and Advanced Life Support: 2020 American Heart Association Guidelines for Cardiopulmonary Resuscitation and Emergency Cardiovascular Care", Circulation, vol. 142, No. 16, Oct. 2020, pp. 366-468.
Perkins, et al., "Cardiac Arrest a nd Cardiopulmonary Resuscitation Outcome Reports: Update of the Utstein Resuscitation Registry Templates for Out-of-Hospital Cardiac Arrest", Resuscitation, vol. 96, Nov. 2015, pp. 328-340.
Rahimi, et al., "Effect of Time to Treatment With Antiarrhythmic Drugs on Return of Spontaneous Circulation in Shock- Refractory Out-of-Hospital Cardiac Arrest", J Am Heart Assoc., vol. 11, No. 6, Mar. 2022, 18 pages.
Santangeli, et al., "Examining the safety of amiodarone", Expert Opin Drug Saf., vol. 11, No. 2, Mar. 2012, pp. 191-214.
Yannopoulos, et al., "Advanced reperfusion strategies for patients with out-of-hospital cardiac arrest and refractory ventricular fibrillation (ARREST): a phase 2, single centre, open-label, randomised controlled trial", Lancet, vol. 396, No. 10265, Dec. 2020, pp. 1807-1816.
Lupton, et al., "Development of a Clinical Decision Rule for the Early Prediction of Shock-Refractory Out-of-Hospital Cardiac Arrest," Resuscitation, Oct. 2022, 8 pages.

(56) References Cited

OTHER PUBLICATIONS

Sashidhar et al., "Machine learning and feature engineering for predicting pulse presence during chest compressions," R Soc Open Sci, vol. 8, No. 11, Nov. 2021, 14 pages.

* cited by examiner

TECHNIQUES FOR PREDICTING AND TREATING REFRACTORY VENTRICULAR FIBRILLATION

CROSS-REFERENCE TO RELATED APPLICATION

This application is a U.S. National Phase Application based on International Patent Application No. PCT/US2023/036321, filed on Oct. 30, 2023, which claims priority to U.S. Provisional App. No. 63/421,901, which was filed on Nov. 2, 2022, each of which is incorporated by reference herein in its entirety.

BACKGROUND

Out-of-hospital cardiac arrest (OHCA) is a leading cause of death, claiming over approximately 300,000 lives each year in the United States (Virani S S, et al. Circulation. 2020; 141: E139-E596). Ventricular fibrillation (VF), an arrhythmia characterized by disorganized electrical activity in the electrocardiogram (ECG), is a common cause of OHCA. Resuscitation from OHCA caused by VF (VF-OHCA) is possible through coordinated administration of cardiopulmonary resuscitation (CPR) to provide circulatory support, electric shock to terminate VF, and medications such as vasopressor to increase perfusion and antiarrhythmics to facilitate sustained defibrillation. CPR in particular is an important treatment which comprises chest compressions (either administered by hand or using an automated chest compression device) and artificial respirations (either administered using bag-mask ventilation or via endotracheal intubation). However, CPR (particularly chest compressions) can cause transient, oscillatory, or chaotic electrical artifacts in the ECG due to motion, perturbation of defibrillator electrodes, and changes in impedance. These chest compression artifacts can obscure the underlying cardiac signal, challenging accurate assessment of the cardiac rhythm. Resuscitation guidelines therefore attempt to compromise the benefit of CPR against the harm of pausing CPR to allow assessment of the ECG.

Specifically, resuscitation guidelines in 2023 follow a graduated protocol whereby emergency medical services (EMS) provide CPR interrupted every 2 minutes to allow rhythm assessment and shock if VF is present (Panchal A R et al., Circulation. 2020; 142: S366-S468). If VF is refractory (e.g., the VF persists or recurs after 2 shocks, often necessitating a third shock), guidelines recommend administration of antiarrhythmics (e.g. amiodarone) after a third shock is given to the patient. The goal of antiarrhythmics in the case of refractory VF is to improve the likelihood of successful defibrillation and help prevent recurrent fibrillation (Panchal A R, et al., Circulation. 2018; 138:e740-e749; Soar J, et al; Resuscitation. 2019; 134:99-103). The rationale for antiarrhythmic treatment in response to refractory VF is supported in part by investigations observing that a greater number of shocks and increased time in VF, which can result from refractory VF, are associated with a lower likelihood of survival (Holmen J, et al., Resuscitation. 2017; 113:33-38; Berdowski J., et al., Circulation. 2010; 122:1101-1108; van Alem A P, et al., Resuscitation. 2003; 59:181-188). Hence, the ability to predict refractory VF in advance of repeated shock failure (e.g. prior to administration of 3 shocks) could enable preemptive interventions targeted at improving the relatively poor outcomes of the refractory VF subgroup. Such therapies for refractory VF might include earlier or increased antiarrhythmic dose administration (Rahimi M, et al., J Am Heart Assoc. 2022; 11:e023958; Dorian P, et al., N Engl J Med. 2002; 346:884-890; Kudenchuk P J, et al., N Engl J Med. 1999; 341:871-878; Cheskes S, et al., Resuscitation. 2020; 157:269-271; Lane D J, et al., Heart. 2022; 108:1777-1783), reconsideration of epinephrine use or reducing its dosage (Sousa J, et al., Am J Cardiol. 1992; 69:509-512; Andersen L W, et al., BMJ. 2016; 353:11577; Evans E, et al., BMJ. 2021; 375:e066534), changes in how shocks are administered (Cheskes S, et al., N Engl J Med. 2022; 387:1947-1956), or expedited hospital-based invasive interventions (Yannopoulos D, et al., Lancet. 2020; 396: 1807-1816; Bartos J A, et al., Circulation. 2020; 141:877-886; Maekawa K, et al., Crit Care Med. 2013; 41:1186-1196; Rob D, et al., Crit Care. 2022; 26:330; Belohlavek J, et al., JAMA. 2022; 327:737-747). By contrast, empiric treatment of all VF OHCA patients using such strategies may unnecessarily expose non-refractory patients to treatments they do not need, introducing potential risk among those unlikely to benefit (Karlis G, et al., Acta Anaesthesiol Scand. 2014; 58:114-122; Santangeli P, et al., Expert Opin Drug Saf. 2012; 11:191-214; Grunau B, et al., JAMA. 2020; 324:1058-1067).

BRIEF DESCRIPTION OF THE DRAWINGS

Some of the drawings submitted herewith may be better understood in color. Applicants consider the color versions of the drawings as part of the original submission and reserve the right to present color images of the drawings in later proceedings.

DETAILED DESCRIPTION

Figure 1:
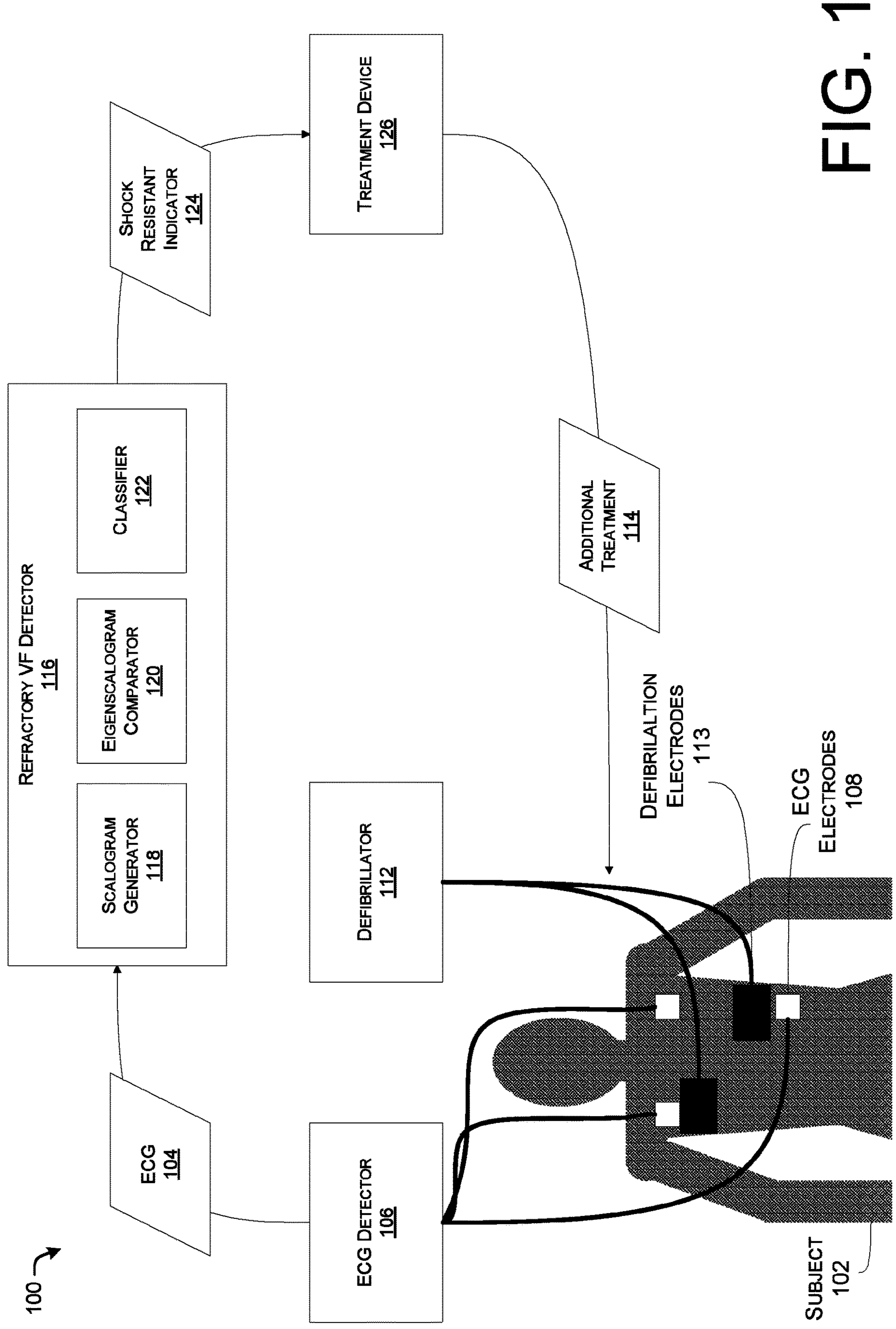
FIG. 1 illustrates an example environment for identifying a shock-resistant heart rhythm using an eigenscalogram-based analysis.

Shock-refractory VF (also referred to as "refractory VF") is a type of VF that recurs or persists even after repeated shocks (e.g., at least two shocks having the same energy and/or shape) are administered to the heart during resuscitation. Specifically, resuscitation guidelines define refractory VF as VF that persists or recurs after 2 shocks, resulting in a total of 3 or more shocks being given to the patient. Previously, there was no automated method to identify (e.g., diagnose) refractory VF without waiting to see whether the VF of a patient would persist after 2 (or more) shocks during resuscitation. However, real-time evaluation of the ECG signal acquired by a defibrillator during resuscitation could offer the potential to predict refractory VF. This disclosure relates to techniques for predicting shock-refractory VF by real-time analysis of the ECG using signal processing, dimensionality reduction, and machine learning (ML). Implementations of this disclosure could enable preemptive clinical strategies to treat refractory VF and in turn improve survival from VF-OHCA.

Various implementations described herein relate to techniques for predicting whether a patient is exhibiting a shock-resistant arrhythmia, such as refractory VF. The term "shock-resistant arrhythmia," and its equivalents, refers to an abnormal heart rhythm (e.g., VF) that persists despite the administration of one or more electrical shocks. According to some cases, various segments of an ECG of the patient are obtained. A first segment of the ECG occurs prior to the administration of an electrical shock to the patient. At least one second segment of the ECG occurs after administration of the electrical shock to the patient. One or more of the segments may occur while the patient is receiving chest compressions.

The ECG segments are compared to a set of representations of standardized characteristics of ECG segments. For instance, the ECG segments are converted into scalograms and the scalograms are compared to a set of eigenscalograms. In various cases, the eigenscalograms are principal components of scalograms from ECG segments of a population of individuals that omit the patient. In some cases, dot products of the patient scalograms and the eigenscalograms from a population of individuals that omit the patient are obtained. These dot products may represent a comparison between the scalograms and the set of eigenscalograms.

According to some implementations, a classifier is used to determine whether the ECG of the patient is indicative of the shock-resistant arrhythmia. For instance, the comparisons (e.g., the dot products) are input into a ML classifier, such as a decision tree, that has been trained based on ECG scalograms obtained from a population of individuals omitting the patient. In some cases, the same ECG segments used to generate the set of eigenscalograms are also used to train the ML classifier. In some examples, different ECG segments are used to generate the set of eigenscalograms and to train the ML classifier. In various examples, the trained ML classifier is used to identify whether the comparisons between a patient's scalograms and eigenscalograms include predictive characteristics that are indicative of a shock-resistant heart rhythm, such as refractory VF.

Various implementations of the present disclosure are directed to improvements in the field of medical devices. Previous techniques for identifying a shock-resistant heart rhythm, such as refractory VF, required the administration of multiple (e.g., 3 or more) electrical shocks to a patient and observing the patient's response to the multiple electrical shocks. In contrast, implementations of the present disclosure enable the identification of a shock-resistant heart rhythm after the administration of a single electrical shock. Accordingly, delays in treating the shock-resistant heart rhythm can be avoided. Furthermore, patient harm from unnecessary electrical shocks (e.g., electrical shocks with limited therapeutic value) can, in some cases, be avoided.

Implementations of the present disclosure will now be described with reference to the accompanying figures.

FIG. 1 illustrates an example environment 100 for identifying a shock-resistant heart rhythm using an eigenscalogram-based analysis. In various cases, the environment 100 is an out-of-hospital environment. For instance, the environment 100 is a non-clinical setting, such as a school, airport, home, or other public space.

In the environment 100, a subject 102 presents with cardiac arrest. In some cases, the subject 102 has unexpectedly collapsed within the environment 100. In some examples, the subject 102 is exhibiting cardiac arrest. The term "cardiac arrest," and its equivalents, may refer to a state in which an individual's heart has ceased pumping blood effectively throughout the body of the individual. Due to the inadequate circulation of oxygenated blood through the body of the subject 102 due to the cardiac arrest, the brain and other vital organs of the subject 102 are at risk of hypoxic injury. In particular cases, the subject 102 has collapsed due to inadequate blood flow to the brain of the subject 102.

Various types of cardiac arrhythmias can result in loss of effective blood flow and cause cardiac arrest. In particular cases, the subject 102 is exhibiting VF. The terms "ventricular fibrillation," "VF," and their equivalents, may refer to a disorganized arrhythmia in which the ventricles contract in an uncoordinated manner, such that the chambers of the heart are unable to effectively pump blood.

According to various cases, an ECG 104 of the subject 102 exhibits the VF. As used herein, the terms "ECG," "EKG," "electrocardiogram," and their equivalents, may refer to data indicative of an electrical signal output by the heart of an individual over time. This electrical signal, in various cases, is generated by depolarization and repolarization of cardiac muscle of the subject 102. In various cases, the ECG 104 is representative of a relative electrical potential energy (e.g., voltage) between multiple electrodes that are disposed on different sides of the heart of the subject 102. In some cases, the ECG 104 is represented by multiple voltage-over-time channels, referred to as "leads," that correspond to the relative potential electrical energy detected using different combinations of electrodes. For instance, the ECG 104 is a single-lead ECG, a 2-lead ECG, a 3-lead ECG, a 12-lead ECG, or a 15-lead ECG.

The ECG 104 is detected by an ECG detector 106 via electrodes 108 that are disposed on the skin of the subject 102. That is, the electrodes 108 are external electrodes. In some cases, the electrodes 108 are adhered to the skin of the subject 102 via an electrically conductive adhesive. The electrodes 108 are electrically coupled to the ECG detector 106. In various cases, the ECG detector 106 includes at least one analog-to-digital converter (ADC) configured to convert one or more voltages detected by the electrodes 108 into digital data that can be further analyzed by at least one processor.

The VF of the subject 102 is apparent in the ECG 104. The ECG 104, for instance, may lack defined P waves, QRS complexes, and T waves. Instead, the VF may be exhibited by disorganized fibrillation waves, which may have different amplitudes and shapes. In some cases, a fundamental frequency of these fibrillation waves may be in a range of 2 to 15 Hz. In various cases, the ECG detector 106 is configured to identify the VF of the subject 102 by analyzing the ECG 104. According to some examples, the VF of the subject 102 is determined by an algorithm that can perform a shock decision. In some cases, the VF of the subject 102 is determined by human visual assessment of the ECG.

In various cases, the VF of the subject 102 can be treated by administering an electrical shock to the heart of the subject 102. The electrical shock is administered, for instance, by a defibrillator 112. Although the ECG detector 106 and the defibrillator 112 are illustrated as different devices in FIG. 1, implementations are not so limited. For instance, the defibrillator 112 may be electrically coupled to the electrodes 108 and may perform the operations of the ECG detector 106. In some cases, the defibrillator 112 includes an automated external defibrillator (AED) or monitor-defibrillator.

In various examples, the electrical shock is a biphasic electrical shock administered by the defibrillator 112 via defibrillation electrodes 113. According to various cases, the defibrillation electrodes 113 are disposed on the skin of the subject 102. For instance, the defibrillation electrodes 113 are adhered to the skin of the subject 102 via a conductive adhesive. Although not specifically illustrated in FIG. 1, in some implementations, the ECG electrodes 108 and the defibrillation electrodes 113 are part of integrated pads, wherein at least one of the ECG electrodes 108 and at least one of the defibrillation electrodes 113 are disposed on the same electrically insulative substrate. The defibrillator 112 may include a power source that charges at least one capacitor with a predetermined charge. The defibrillator 112 may subsequently discharge the capacitor(s) to the defibrillation electrodes 113. The electrical shock, in some cases, is biphasic. The electrical shock may have an energy in a range of 120 Joules (j) to 360 joules, or 120 to 200 J.

According to some examples, the VF of the subject 102 is terminated after administration of a single electrical shock. However, in some cases, the VF of the subject 102 persists (e.g., is continuous and does not terminate) or recurs (terminates and then subsequently resumes) after multiple electrical shocks. The terms “refractory VF,” “shock-refractory VF,” and their equivalents, as used herein, may refer to a type of shock-resistant VF that persists or recurs after the administration of more than a threshold number of electrical shocks, wherein the threshold number is greater than one. For example, the refractory VF may persist or recur after administration of two electrical shocks, three electrical shocks, four electrical shocks, five electrical shocks, or a greater number of electrical shocks.

In many cases in which the subject 102 has refractory VF, the VF of the subject 102 may cease after the subject 102 receives an additional treatment 114. For example, the VF of the subject 102 may resolve after the subject 102 is administered a vasopressor (e.g., epinephrine), an anti-arrhythmic (e.g., amiodarone), or any combination thereof. In some cases, the VF of the subject 102 may persist after administration of one or more unnecessary medications, such as a vasopressor. According to some cases, the additional treatment 114 includes withholding administration of a vasopressor. In some cases, the additional treatment 114 includes administration of cardiac catheterization. During cardiac catheterization, a catheter may be inserted into at least one chamber and/or vessel of the heart of the subject 102. In some examples, the additional treatment 114 includes administration of extracorporeal membrane oxygenation (ECMO). ECMO, for instance, is a technique for drawing blood from the body, performing artificial oxygenation on the blood using a membrane oxygenator, removing carbon dioxide from the blood, and administering the oxygenated blood back to the body.

In some instances, the refractory VF of the subject 102 can resolve if the subject 102 is administered a different type of electrical shock. For example, the additional treatment 114 may include a subsequent electrical shock that has a higher energy level than the initial electrical shock administered by the defibrillator 112. In some cases, the additional treatment 114 includes a subsequent electrical shock that is administered at a different vector than the initial electrical shock administered by the defibrillator 112. The term “vector,” and its equivalents, may refer to a direction with respect to an axis of the heart. For example, the initial electrical shock may be administered at a first vector (e.g., an anterior-lateral placement of the defibrillation electrodes 113) and the subsequent electrical shock may be administered at a second vector (e.g., an anterior-posterior placement of the defibrillation electrodes 113).

However, administration of the additional treatment 114 is delayed to the subject 102 if the refractory VF is identified after the administration of 3 or more electrical shocks. In general, rescuers are advised to administer chest compressions between the administration of electrical shocks by a defibrillator. For instance, the chest compressions are administered for period of 2 minutes. These chest compressions, in various cases, are used to generate some blood circulation in the body of the subject 102, so that the brain and vital organs receive some oxygen during the cardiac arrest. In various cases, rescuers prioritize the administration of chest compressions during cardiac arrest, in order to prevent severe and irreversible hypoxic injury of the subject 102. The time periods in which chest compressions are administered, however, delay the administration of the electrical shocks. Thus, in various cases in which a rescuer follows accepted resuscitation guidelines, it can take minutes (e.g., 5 or 10 minutes) before the subject 102 receives three electrical shocks during a conventional rescue event. As a result, a conventional technique for identifying refractory VF can leave the subject 102 in VF for an extended period of time (e.g., 5 or 10 minutes), which may cause the subject 102 to suffer from a harmful interval with insufficient blood circulation causing neurological damage, and which also may subject the subject 102 to multiple electrical shocks with limited therapeutic value, which may cause burns and other harm to the subject 102.

In various implementations of the present disclosure, the refractory VF of the subject 102 can be identified prior to the defibrillator 112 administering a threshold number (e.g., three or more) shocks to the subject 102. In various cases, a refractory VF detector 116 is configured to identify the refractory VF by analyzing segments of the ECG 104. Although illustrated separately, the refractory VF detector 116 may be integrated within the ECG detector 106 and/or the defibrillator 112, in some implementations.

For example, the segments of the ECG 104 include a pre-shock segment that occurs prior to the administration of an initial electrical shock administered to the subject 102 by the defibrillator 112. In some cases, the segments of the ECG 104 include at least one post-shock segment that occurs after the administration of the initial electrical shock administered to the subject 102 by the defibrillator 112.

The refractory VF detector 116 includes a scalogram generator 118 configured to generate scalograms of the segments of the ECG 104. The term "scalogram," and its equivalents, refers to an image that is representative of wavelet-transformed data. The term "image," and its equivalents, refers to multi-dimensional array of discrete elements representing different areas or volumes, wherein the discrete elements include values representing intensities and/or gray levels associated with the corresponding areas or volumes. For instance, a two-dimensional (2D) image may include a 2D array of pixels, wherein each pixel corresponds to a discrete portion of an area being represented and each pixel is defined by one or more values that represent one or more intensities of one or more colors. In some examples, a color 2D image is defined according to three color channels (e.g., red, green, and blue (RGB)), such that each pixel includes three values respectively representing an amount of color of each channel being represented by the pixel.

In various cases, the scalograms are generated by performing a wavelet transform on the segments of the ECG 104. In various cases, the term "wavelet transform" refers to a mathematical process by which a function or dataset is convolved with one or more wavelets to produce wavelet coefficient values. For example, the wavelet transform may include a discrete wavelet transform, a continuous wavelet transform, a complex wavelet transform, a Haar wavelet transform, a Doubechies wavelet transform, a Morlet wavelet transform, a Gabor wavelet transform, or any combination thereof. In particular cases, the scalograms are generated using a Morlet wavelet transform to calculate wavelet coefficient values which define the pixel values within a scalogram image. According to some cases, wavelet coefficient values are first generated using a complex Morlet wavelet transform and then modified by calculating the magnitude envelope of the wavelet coefficient values. In various cases, the scalograms are generated by convolving wavelets (e.g., Morlet wavelets) corresponding to predetermined center frequencies with segments of the ECG 104. The center frequencies may be logarithmically spaced, in various examples.

In various implementations, the wavelet-transformed data (e.g. wavelet coefficient values from the segments of the ECG 104) can be further modified. According to some cases, the wavelet-transformed data is normalized. According to some cases, the wavelet-transformed data is normalized separately within each set of wavelet coefficients generated from convolution with a wavelet of a specific frequency. For example, a maximum, median, or mean wavelet coefficient magnitude is calculated for coefficients generated from a wavelet with a specific center frequency, and these coefficients are divided by their calculated maximum, median, or mean magnitude. According to various cases, the median magnitude is used for segments of the ECG 104 that omit a chest compression artifact. In some examples, the maximum magnitude is used for segments of the ECG 104 that include a chest compression artifact. In some examples, the wavelet-transformed data is trimmed into one or more frequency ranges. For example, a wavelet-transformed preshock segment of the ECG 104 may be trimmed to a frequency range that is between about 2 Hz and about 35 Hz, or between about 5 Hz and about 40 Hz. In various cases, each wavelet-transformed postshock segment of the ECG 104 is trimmed to a frequency range that is between about 5 Hz and about 35 Hz, or between about 10 Hz and about 30 Hz. In some examples, the scalograms themselves are trimmed to any of these frequency ranges.

The scalograms may be generated by converting the data resulting from the wavelet transformations of the segments of the ECG 104 into images. In the scalograms, for instance, a horizontal axis represents time, a vertical axis represents frequency, and pixel values represent magnitude.

The refractory VF detector 116 also includes an eigenscalogram comparator 120 configured to generate comparisons between the scalograms and a stored set of eigenscalograms. The term "eigenscalogram," and its equivalents, may refer to an image representing a set of eigenvectors that represent a low-rank approximation of multiple scalograms. In various cases, the eigenscalograms are generated (e.g., by the eigenscalogram comparator 120) prior to the detection of the ECG 104. For example, the set of eigenscalograms may be generated by performing principal component analysis (PCA) on a set of training scalograms derived from multiple ECG segments omitting the segments of the ECG 104. In various cases, the set of eigenscalograms are generated based on training scalograms generated based on multiple segments of ECGs obtained from multiple individuals in a population that omits the subject 102. In various cases, each training scalogram is converted to a vector by concatenating its pixel rows. A matrix (X) containing the vectors of the training scalograms is generated, such that each column of the matrix (X) represents a different training scalogram. In some cases, the matrix X is subtracted by its mean value. A diagonal matrix of singular values (S), a matrix of columns of left singular vectors (U), and a matrix of columns of right singular vectors (V) are generated based on a matrix decomposition of X in accordance with the following Equation:

$$X = USV^* \quad (1)$$

where in this equation * indicates a complex conjugate transpose.

The matrix (U) contains multiple eigenscalograms, including the optimized set of eigenscalograms utilized by the eigenscalogram comparator 120. In various cases, the eigenscalogram comparator 120 stores the set of eigenscalograms used for generating the comparisons. Multiple eigenscalograms may be utilized, such as two, three, four, five, six, seven, eight, nine, ten, twenty, thirty, forty, fifty, or more eigenscalograms.

In various implementations, the scalograms of the ECG 104 are compared to the eigenscalograms. Each scalogram, for instance, may be represented as a combination of the set of eigenscalograms, or otherwise represented in a new coordinate space based on similarity to the set of eigenscalograms. In particular, a weight representing the similarity between the scalogram and each eigenscalogram can be determined, such that the scalogram is represented as a set of weights corresponding to the set of eigenscalograms. In some instances, dot products of the scalograms and the eigenscalograms are generated. In some instances, the eigenscalograms are each divided by a singular value from the matrix S prior to the dot product operation. According to various cases, the eigenscalogram comparator 120 determines the comparisons (e.g., weights and/or dot products) of each scalogram representing the pre- and postshock segments of the ECG 104 with the eigenscalograms.

A classifier 122 within the refractory VF detector 116 is configured to determine, based on the comparisons, whether the ECG 104 is indicative of refractory VF. According to various implementations, the classifier 122 includes one or more machine learning (ML) models. The terms "machine learning model," "ML model," and their equivalents, may refer to a computer model that identifies patterns in training data by optimizing one or more parameters in view of the training data, such that the computer model may identify the patterns in additional data using the optimized parameter(s). For instance, the classifier 122 may include, for instance, decision trees, support vector machines (SVMs), k-nearest neighbor models, logistic regression models, random forest models, or any combination thereof.

In various cases, the classifier 122 is pre-trained. For example, one or more parameters of the classifier 122 have been previously optimized based on training data. In some cases, the classifier 122 is trained using supervised learning. For example, the training data may include example inputs (e.g., vectors representing weights comparing example ECG scalograms to the eigenscalograms, dot products of the example ECG scalograms and the eigenscalograms, etc.) and example outputs (e.g., labels indicating whether example ECG segments used to generate the example ECG scalograms are indicative of refractory VF). The parameters of the classifier 122 may be modified until a loss (e.g., a difference or discrepancy) between the outputs of the classifier 122 when the example inputs are input into the classifier 122, and the example outputs, is minimized. After the classifier 122 is trained, it can accurately output a classification of the ECG 104 as indicative of refractory VF by receiving the comparisons of the scalograms of the ECG 104 and the eigenscalograms as an input dataset.

The refractory VF detector 116, in various cases, is configured to output a shock resistant indicator 124 that conveys whether the ECG 104 is indicative of refractory VF. The shock resistant indicator 124, in various implementations, is output from the classifier 122 based on the input dataset. In some examples, the refractory VF detector 116 outputs a signal including the shock resistant indicator 124. In some cases, the refractory VF detector 116 transmits a communication signal including the shock resistant indicator 124 to an external device.

According to various implementations, the shock resistant indicator 124 is received by a treatment device 126. The treatment device 126 is configured to administer the additional treatment 114 to the subject 102, in various cases. For example, the treatment device 126 is a defibrillator (e.g., the defibrillator 112) configured to administer the subsequent electrical shock at a different energy level and/or vector than the initial electrical shock administered by the defibrillator 112. In some cases, the treatment device 126 includes multiple defibrillators (e.g., including the defibrillator 112) configured to administer a double-sequential defibrillation (DSD) therapy to the subject 102. In some examples, the treatment device 126 includes a drug delivery system configured to administer an antiarrhythmic agent to the subject 102.

Figure 2:
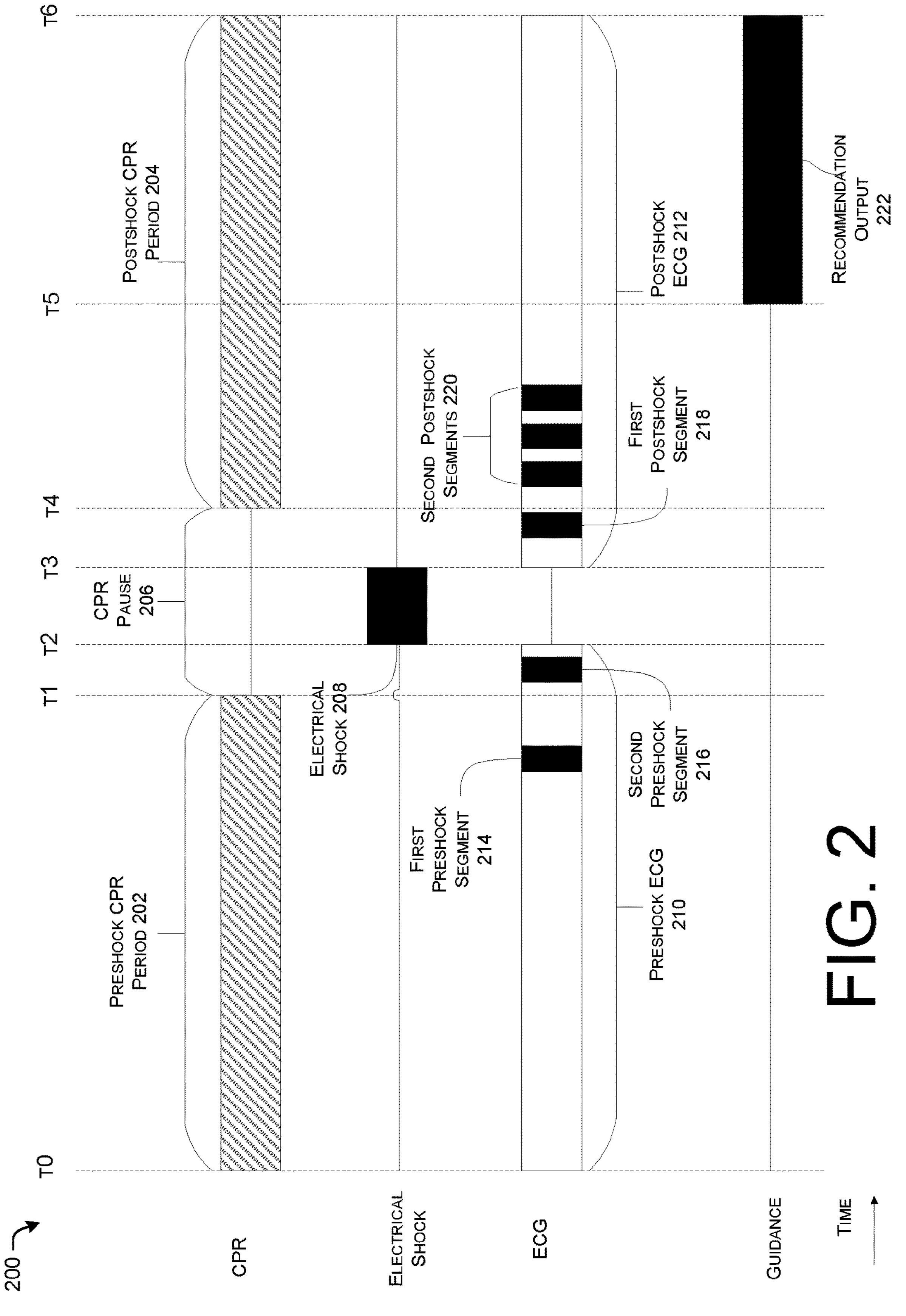
FIG. 2 illustrates a timing diagram associated with a technique for identifying refractory VF shortly after administration of a single electrical shock.

FIG. 2 illustrates a timing diagram 200 associated with a technique for identifying refractory VF shortly after administration of a single electrical shock. In the timing diagram 200, a direction extending from left to right corresponds to an increase in time. Specific time points are depicted in the timing diagram 200, including t0, t1, t2, t3, t4, 15, and t6.

The timing diagram 200 depicts CPR administration to a subject. In particular, chest compressions are administered to the subject during a preshock CPR period 202 and a postshock CPR period 204. The preshock CPR period 202 extends from t0 to t1. The postshock CPR period 204 extends from t4 to t6. In some cases, the preshock CPR period 202 extends for (e.g., t1–t0 is) about two minutes. In various examples, the postshock CPR period 204 extends for (e.g., t6–t4 is) about two minutes. A CPR pause 206 extends between the preshock CPR period 202 and the postshock CPR period 204. The CPR pause 206 begins at t1 and ends at t4. During the CPR pause 206, chest compressions are not administered to the subject.

The timing diagram 200 also depicts the time at which an electrical shock 208 is administered to the subject. The electrical shock 208 is administered to the heart of the subject during the CPR pause 206. For instance, the electrical shock 208 is administered from t2 to t3. The electrical shock 208 may be an initial electrical shock administered to the subject during a rescue event. For example, the electrical shock 208 is the first electrical shock administered to the subject after the subject has exhibited VF.

The timing diagram 200 defines portions of an ECG detected from the subject. For instance, the ECG includes a preshock ECG 210 and a postshock ECG 212. The preshock ECG 210 extends from t0 to t2. The postshock ECG 212 extends between t3 and t6. In various cases, VF is present in at least a portion of the preshock ECG 210, such that the electrical shock 208 is indicated as a treatment for the VF. The preshock ECG 210 can be defined by various segments, such as a first preshock segment 214 and a second preshock segment 216. The first preshock segment 214, in various cases, may be defined at an interval before the preshock CPR period 202 ends at t2, such that the first preshock segment 214 includes a chest compression artifact. The postshock ECG 212, in various cases, includes a first postshock segment 218 and multiple second postshock segments 220. The second postshock segments 220 are defined during time segments occurring after t5, such that the second postshock segments 220 may include a chest compression artifact. Notably, implementations of the present disclosure utilize postshock segments with and/or without a chest compression artifact. Although FIG. 2 illustrates three of the second postshock segments 220, in some cases, more than three segments may be included in the second postshock segments 220.

In various implementations of the present disclosure, it may be determined whether the subject has refractory VF by analyzing one or more preshock segments (e.g., the first preshock segment 214 and/or the second preshock segment 216) and one or more postshock segments (e.g., the first postshock segment 218 and/or at least one of the second postshock segments 220). In various cases, the segments of the ECG are converted to scalograms and compared to a set of eigenscalograms. Based on the comparisons between the scalograms and the eigenscalograms, a classifier may predict whether the VF depicted in the preshock ECG is refractory VF. Thus, the classifier may determine whether the subject is predicted to have refractory VF, and this determination may be made prior to the subject receiving multiple electrical shocks.

According to some cases, a recommendation 222 may be generated based on whether the VF is refractory VF. For instance, the recommendation 222 is output before the postshock CPR period 204 ceases at t6. In various cases, the recommendation 222 is output as early as t5. Notably, the recommendation 222 is output before the subject has received multiple electrical shocks. Accordingly, a rescuer may take action to treat the refractory VF before multiple electrical shocks are administered to the subject.

In some examples, the recommendation 222 may include a warning about the refractory VF. For instance, a display may visually present an indication that the subject is likely to have refractory VF.

In some cases, the recommendation 222 includes an instruction to administer an additional treatment to the subject. For example, the recommendation 222 may include an instruction to administer a therapeutic agent that will mitigate the refractory VF. In some cases, the recommendation 222 includes an instruction to refrain from administering a treatment to the subject in view of the refractory VF. For example, the recommendation 222 may instruct a rescuer to refrain from administering a vasopressor to the subject due to the potential proarrhythmic effects of vasopressor.

According to some examples, the recommendation 222 includes an instruction to administer another electrical shock to the subject. The other electrical shock may be different from the electrical shock 208 in one or more respects. The recommendation 222 may include an instruction to administer the other electrical shock with a higher energy level and/or a different vector than the electrical shock 208. For instance, the recommendation 222 may instruct the rescuer to increase the energy level of a defibrillator being used to monitor and/or treat the subject and/or may instruct the rescuer to change the position of defibrillation electrodes on the body (e.g., chest and/or back) of the subject. In some cases, the recommendation 222 may include an instruction to administer a DSD treatment that includes multiple electrical shocks within a short period of time (e.g., within 2 seconds of each other).

Although not specifically illustrated in FIG. 2, in various cases, the rescuer can administer a treatment to the subject and resolve the refractory VF relatively quickly after the subject enters cardiac arrest. In various implementations described herein, the treatment is administered without the (e.g., prior to) administration of multiple (e.g., two, three, four, etc.) electrical shocks to the subject.

Figure 3:
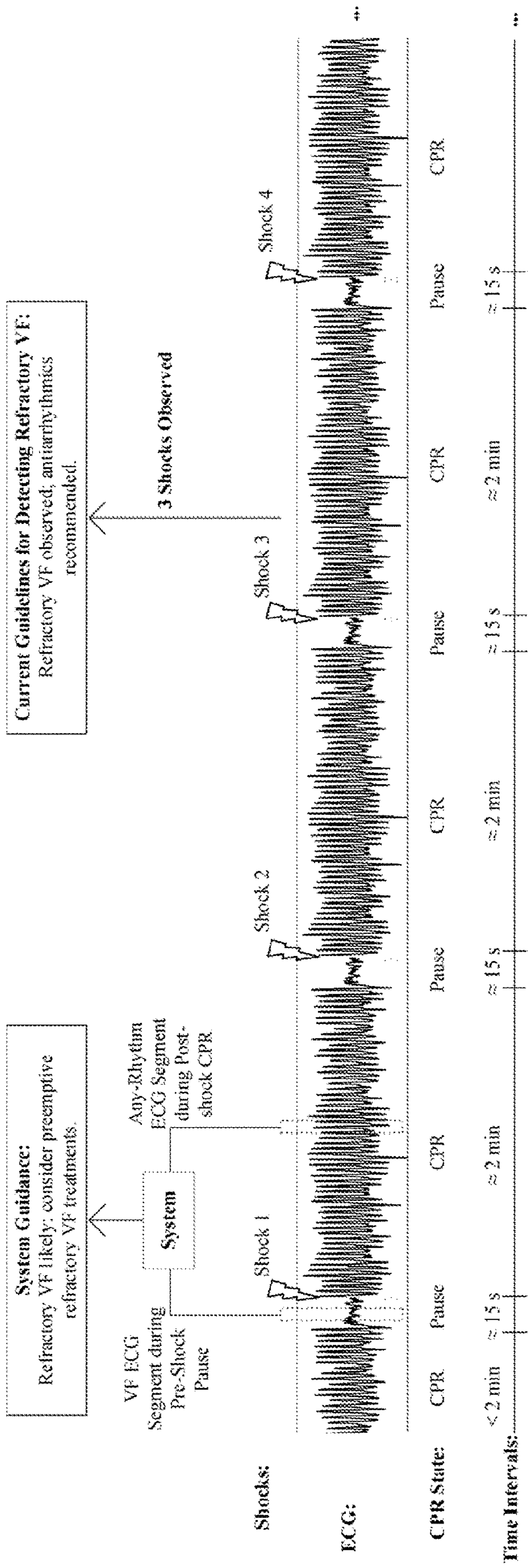
FIG. 3 illustrates an example timing diagram in which refractory VF can be identified based on a single preshock segment and a single postshock segment.

FIG. 3 illustrates an example timing diagram in which refractory VF can be identified based on a single preshock segment and a single postshock segment. Specifically, FIG. 3 illustrates the timing of shocks, ECG, and CPR state during an example rescue event.

During the event, the ECG is detected from a subject. The subject is administered four shocks (shock 1, shock 2, shock 3, and shock 4) during the event. Between shocks, the subject is administered CPR in 2-minute-long CPR periods, in accordance with current resuscitation guidelines. The shocks are administered during CPR pauses, that occur for about 5 seconds to about 30 seconds between CPR periods. Current guidelines recommend antiarrhythmic administration after shock 3. One potential application of the proposed method might include an earlier antiarrhythmic recommendation on the basis of a prediction of refractory VF. The ECG shown is a caricature illustration and is not to scale. CPR indicates cardiopulmonary resuscitation; and VF, ventricular fibrillation.

The subject has refractory VF. Accordingly, the subject may exhibit VF before and after shock 1, after shock 2, and after shock 3. That is, shock 1, shock 2, and shock 3 are not effective at resolving the VF of the subject. In various cases, the VF of the subject is continuous throughout the rescue event. In an example, the clinician could initiate administration of an antiarrhythmic agent to the subject after shock 3.

Under some current guidelines, a clinician could identify that the subject has refractory VF after observing VF following shock 3. However, it would be advantageous to predict whether the subject has refractory VF before shock 2 is administered. This could enable the clinician to administer the antiarrhythmic agent earlier, thereby potentially shortening the time at which the VF of the subject persists, and potentially reducing the subject's risk of hypoxic injury or brain death due to the refractory VF.

In various implementations described herein, a system predicts whether the subject has refractory VF based on a preshock segment of the ECG and a postshock segment of the ECG. The preshock segment is detected during a time interval that occurs prior to the administration of shock 1. In various cases, the preshock segment is detected during a CPR pause in which shock 1 is administered. The postshock segment is detected during a time interval that occurs after the administration of shock 2.

In various cases, the system performs an eigenscalogram analysis on the preshock segment and the postshock segment. For example, the system generates a scalogram based on the preshock segment and a scalogram based on the postshock segment. The system compares the preshock scalogram to a set of specific preshock eigenscalograms, and compares the postshock scalogram to a set of specific postshock eigenscalograms, which in some examples, may be different from the preshock eigenscalograms. Based on the comparisons, the system can classify the ECG as being indicative of refractory VF. As a result, the system can output a warning or instruction to consider preemptive refractory VF treatments before shock 2 is administered.

Figure 4:
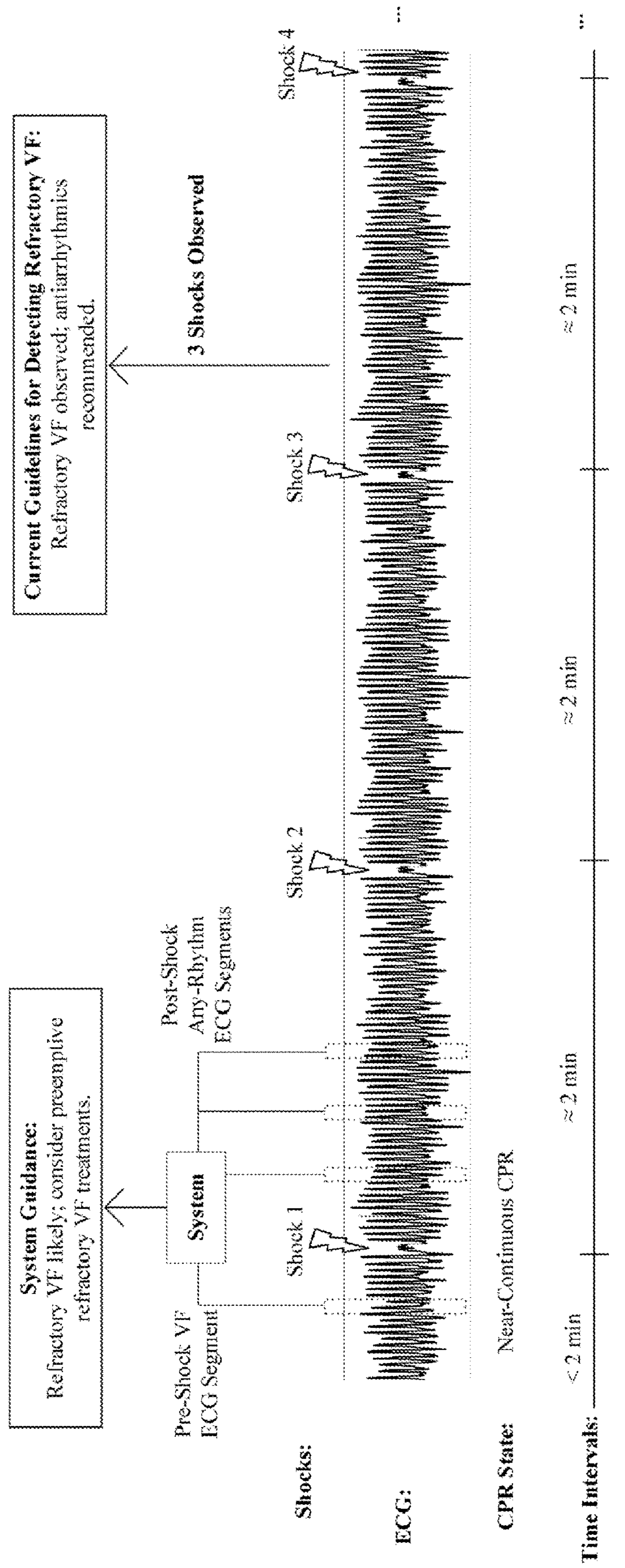
FIG. 4 illustrates an example timing diagram in which refractory VF can be identified based on a single preshock segment and multiple postshock segments.

FIG. 4 illustrates an example timing diagram in which refractory VF can be identified based on a single preshock segment and multiple postshock segments in a scenario where CPR is administered continuously or substantially continuously. Specifically, FIG. 4 illustrates the timing of shocks, ECG, and CPR state during an example rescue event. During the event, the ECG is detected from a subject. The subject is administered four shocks (shock 1, shock 2, shock 3, and shock 4) during the event. Between shocks, the subject is administered CPR in 2-minute-long CPR periods in accordance with some current resuscitation guidelines, but in contrast to current resuscitation guidelines, CPR is not paused to allow analysis of the ECG without CPR. Unlike the example illustrated in FIG. 3, the shocks illustrated in FIG. 4 may be either administered during very short (e.g. 5 seconds) CPR pauses, or administered during uninterrupted CPR. For instance, the CPR may be administered by a defibrillator that is resistant to damage during administration of the shocks. Current guidelines recommend antiarrhythmic administration after shock 3. One potential application of the proposed method might include an earlier antiarrhythmic recommendation on the basis of a prediction of the patient requiring a total of 3 or more shocks. The ECG shown is an illustration only, and is not to scale.

The subject has refractory VF. Accordingly, the subject may exhibit VF before and after shock 1, after shock 2, and after shock 3. That is, shock 1, shock 2, and shock 3 are not effective at resolving the VF of the subject. In various cases, the VF of the shock-refractory subject is continuous throughout the rescue event. In various cases, the VF of the shock-refractory subject could be successfully terminated following one or more shocks and then recur. In an example, the clinician could initiate administration of an antiarrhythmic agent to the subject after shock 3.

Under some current guidelines, a clinician could identify that the subject has refractory VF after observing VF following shock 2 or observing that the defibrillator had administered a third shock. However, it would be advantageous to predict whether the subject has refractory VF before shock 2 is administered. This could enable the clinician to administer the antiarrhythmic agent earlier, thereby potentially shortening the time at which the VF of the subject persists and increasing the effectiveness of subsequent shock, potentially reducing the subject's risk of hypoxic injury or brain death due to the lack of blood flow during refractory VF.

In various implementations described herein, a system predicts whether the subject has refractory VF based on a preshock segment of the ECG and multiple postshock segments of the ECG. The preshock segment is detected during a time interval that occurs prior to the administration of shock 1. The postshock segments are detected during a time interval that occurs after the administration of shock 2. In various cases, the preshock segment and the postshock sgements are detected during time intervals in which the subject is administered CPR. Thus, the segments may include a chest compression artifact.

In various cases, the system performs an eigenscalogram analysis on the preshock segment and the postshock segments. For example, the system generates scalograms based on the preshock segment and the postshock segments. The system compares the scalograms to a set (or sets) of eigenscalograms. Based on the comparisons, the system can classify the ECG as being indicative of refractory VF. As a result, the system can output a warning or instruction to consider preemptive refractory VF treatments before shock 2 is administered.

Figure 5:
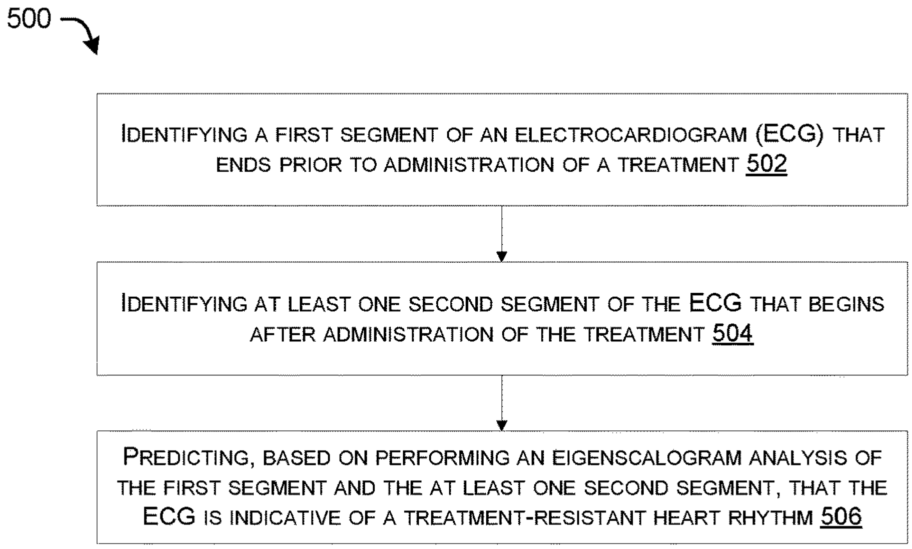
FIG. 5 illustrates an example process for identifying whether a subject has a heart rhythm that is resistant to a treatment.

FIG. 5 illustrates an example process 500 for identifying whether a subject has a defibrillation-resistant heart rhythm. The process 500 may be performed by an entity including at least one processor, at least one computing device (e.g., one or more servers), a medical device, a defibrillator, a patient monitor, or any combination thereof.

At 502, the entity identifies a first segment of an ECG that ends prior to the administration of a treatment. In various cases, the ECG is detected from a subject, such as a patient, using a sensor. For instance, the sensor includes multiple ECG electrodes disposed on the chest of the subject, a circuit configured to detect a relative voltage between at least one pair of the ECG electrodes, and an analog-to-digital converter (ADC) configured to generate a digital signal indicative of the voltage over time.

In various cases, the first segment of the ECG is detected during a first time interval that begins and ends prior to the administration of the treatment. In various cases, the subject is experiencing a medical emergency, such as cardiac arrest. For instance, the subject may be receiving CPR (e.g., chest compressions, and in some instances, artificial respirations) during the first time interval, such that the first segment of the ECG includes a chest compression artifact. In some cases, the artifact is reduced and/or removed from the first segment of the ECG using one or more filters. In some cases, the subject receives CPR prior to the administration of the treatment. In some examples, the first time interval occurs during a CPR pause (e.g., after chest compressions cease being administered to the subject). For instance, the first time interval may begin within one minute before the administration of the treatment. In various examples, the first segment of the ECG has a length of 1 second, 5 seconds, 10 seconds, 30 seconds, or one minute.

According to some examples, the first segment of the ECG is indicative of a condition that may be resolved using the treatment. For instance, the first segment of the ECG is indicative of a condition (e.g. VF) that is treatable by administration of an electrical shock to the subject. The entity, in some cases, analyzes the first segment of the ECG in order to detect the condition. In some cases, the entity is configured to recommend that the treatment (e.g., an electrical shock) be administered to the subject. In some examples, the entity is configured to administer the treatment to the subject. For example, the entity may output the electrical shock to defibrillation electrodes disposed on the chest of the subject.

In some cases, the treatment represents an initial treatment administered to the subject. For example, the treatment may include the first electrical shock administered to the subject since the start of the detection of the ECG of the subject by the entity. In some examples, the treatment may be the first electrical shock administered to the subject since the ECG electrodes were placed on the chest of the subject. In some cases, the treatment is the first treatment administered to the subject after the subject presented with cardiac arrest.

At 504, the entity identifies at least one second segment of the ECG that begins after administration of the treatment. In some cases, the second segment(s) include one, two, three, four, five, or more non-overlapping segments of the ECG.

In various cases, the second segment(s) are detected during at least one second time interval that begins and ends after the administration of the treatment. For example, the second time interval(s) end within one minute after administration of the treatment to the subject. The second time interval(s) may each have a length in a range of 1 second to 20 seconds. The second time interval(s) may occur during the administration of CPR to the subject, such that the second segment(s) include a chest compression artifact. In some cases, the entity removes and/or reduces the chest compression artifact in the second segment(s). In some cases, one or more of the second time interval(s) occur during a CPR pause. In particular cases, the second segment(s) include a segment beginning 1 to 20 seconds after administration of the treatment, a segment beginning 20 to 40 seconds after administration of the treatment, a segment beginning 40 to 60 seconds after administration of the treatment, or any combination thereof.

At 506, the entity predicts, based on performing an eigenscalogram analysis of the first segment and the at least one second segment, that the ECG is indicative of a treatment-resistant heart rhythm. In various cases, the entity predicts whether the subject has refractory VF in view of the eigenscalogram analysis.

In various cases, the entity converts the first segment and the second segment(s) to scalograms. For example, the entity generates the scalograms using a wavelet transform. The scalograms, for instance, include images indicative of the first segment and the second segment(s). In some cases, the entity further modifies one or more of the scalograms. For example, the entity normalizes wavelet coefficient magnitude values of one or more of the scalograms. In some cases, the wavelet coefficient magnitude value normalization is performed separately within each set of coefficients generated from convolution with a single wavelet having a specific center frequency. In some cases, the entity normalizes scalograms representing segments of the ECG that were detected during the administration of CPR to the subject. In various cases, the normalization is performed by dividing, for coefficients within each individual scalogram frequency, wavelet coefficient magnitude values of the scalograms by at least one of the maximum, median, or mean wavelet coefficient magnitude. In some cases, the median is used for normalization of scalograms based on ECG segments detected during a CPR pause. In various cases, the maximum is used for normalization of scalograms based on ECG segments detected during CPR administration. In some examples, the scalograms are trimmed to one or more frequency ranges. For instance, the scalogram based on the first segment is trimmed to a first frequency range (e.g., 2 to 35 Hz, 5 to 30 Hz, or the like). In some cases, the scalogram(s) based on the second segment are trimmed to a second frequency range (e.g., 5 to 35 Hz, 10 to 30 Hz, or the like).

According to various implementations, the entity generates comparisons of the scalograms and a set of eigenscalograms. For example, the entity generates, for each scalogram, a set of weights corresponding to the contribution and/or representation of each eigenscalogram to the scalogram. In some cases, the entity generates dot products of the scalograms and the eigenscalograms.

According to some examples, the entity uses a classifier to classify the comparisons between the scalograms and the eigenscalograms. For instance, the classifier includes at least one ML model that is configured to output an indication of whether the ECG is indicative of the treatment-resistant condition based on receiving input data including the comparisons. In some cases, the classifier includes a trained random forest, SVM, or k-nearest neighbor model. For instance, the ML model(s) are pre-trained in a supervised fashion based on other ECG-based scalogram comparisons and labels indicating whether the ECG-based scalograms are obtained from individuals who have the treatment-resistant heart rhythm. In some cases, the entity and/or classifier generates data indicating whether the ECG is indicative of the treatment-resistant heart rhythm.

Optionally, the entity performs additional actions based on determining whether the subject has the treatment-resistant condition. In some cases, the entity outputs a signal (e.g., to an external device, to a user, or the like) that specifies whether the ECG is indicative of the treatment-resistant heart rhythm. In some implementations, in cases where the entity determines that the ECG is indicative of the treatment-resistant heart rhythm, the entity outputs a signal (e.g., to the external device, to the user, or the like) including an instruction to administer an additional treatment to the subject. In various cases, the additional treatment may have a greater chance of resolving the treatment-resistant heart rhythm than the original treatment (e.g., the electrical shock) administered to the subject. For instance, the instruction may recommend administering an antiarrhythmic medication to the subject, administering a subsequent electrical shock at a different vector than the original electrical shock, administering a DSD treatment, administering a cardiac catheterization treatment, refraining from administering a vasopressor, or administering ECMO to the subject. In some examples, the entity itself outputs the additional treatment to the subject.

In various implementations, the entity outputs the signal(s) and/or administers the additional treatment within two minutes of the administration of the original treatment (e.g., the original electrical shock). In some cases, the entity outputs the signal(s) before a subsequent electrical shock is administered to the subject. Various implementations of the present disclosure enable therapies to be administered to treat the treatment-resistant heart rhythm of the subject before the subject receives multiple (e.g., two or more) electrical shocks. Thus, implementations of the present disclosure can enable rapid treatments to the subject.

Figure 6:
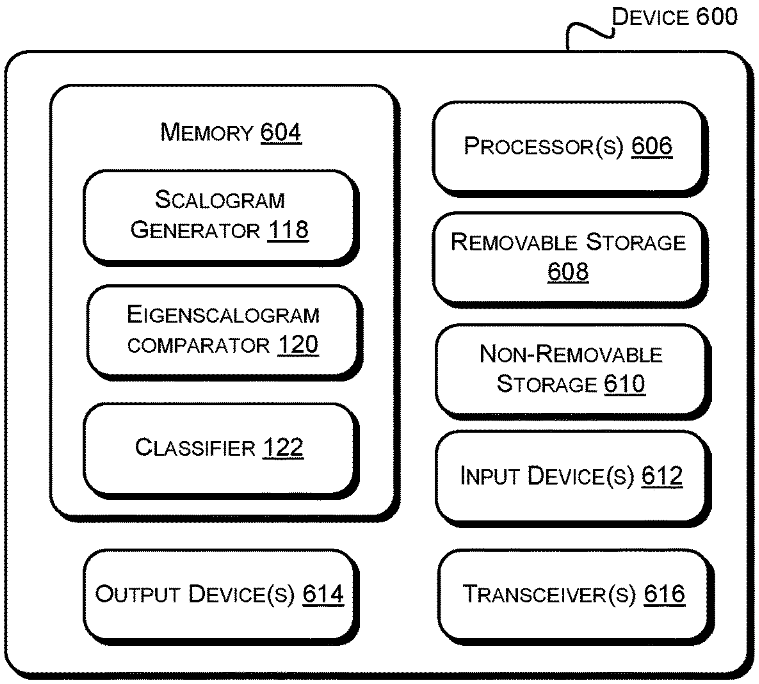
FIG. 6 illustrates an example of a device configured to perform various methods and functions described herein.

FIG. 6 illustrates an example of a device 600 configured to perform various methods and functions described herein. The device 600 may be at least a part of the ECG detector 106, the defibrillator 112, the refractory VF detector 116, the treatment device 126, or any combination thereof, as illustrated in FIG. 1. The device 600 includes any of memory 604, processor(s) 606, removable storage 608, non-removable storage 610, input device(s) 612, output device(s) 614, and transceiver(s) 616.

The memory 604 may include (e.g., store) one or more components, such as instruction(s), program(s), database(s), software, operating system(s), models, etc. In some implementations, the component(s) include instructions that are executed by processor(s) 606 and/or other components of the device 600. For example, the memory 604 includes instructions for performing functions of the scalogram generator 118, the eigenscalogram comparator 120, the classifier 122, or any combination thereof.

In some embodiments, the processor(s) 606 include a central processing unit (CPU), a graphics processing unit (GPU), or both CPU and GPU, or microcontroller, or other processing unit or component known in the art.

The device 600 may also include additional data storage devices (removable and/or non-removable) such as, for example, magnetic disks, optical disks, or tape. Such additional storage is illustrated in FIG. 6 by removable storage 608 and non-removable storage 610. Tangible computer-readable media can include volatile and non-volatile, removable and non-removable media implemented in any method or technology for storage of information, such as computer readable instructions, data structures, program modules, or other data. The memory 604, the removable storage 608, and the non-removable storage 610 are all examples of computer-readable storage media. Computer-readable storage media include, but are not limited to, Random Access Memory (RAM), Read-Only Memory (ROM), Electrically Erasable Programmable Read-Only Memory (EEPROM), flash memory, or other memory technology, Compact Disk Read-Only Memory (CD-ROM), Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device 600. Any such tangible computer-readable media can be part of the device 600.

The device 600 may be configured to communicate over a telecommunications network using any common wireless and/or wired network access technology. Moreover, the device 600 may be configured to run any compatible device Operating System (OS), including but not limited to, Microsoft Window, Google Android, Apple OS, Linux, as well as any other common OS.

The device 600 also can include input device(s) 612, such as a keypad, a cursor control, a touch-sensitive display, voice input device, etc. In some cases, the input device(s) 612 include one or more sensors, electrodes, ADCs, or other circuitry to detect physiological parameters. The device 600 further includes output device(s) 614 such as a display, speakers, printers, etc. In some cases, the output device(s) 614 include power sources, circuits, electrodes, or other elements configured to administer medical treatments.

As illustrated in FIG. 6, the device 600 also includes one or more wired or wireless transceiver(s) 616. For example, the transceiver(s) 616 can include a network interface card (NIC), a network adapter, a Local Area Network (LAN) adapter, or a physical, virtual, or logical address to connect to various network components, for example. To increase throughput when exchanging wireless data, the transceiver(s) 616 can utilize multiple-input/multiple-output (MIMO) technology. The transceiver(s) 616 can comprise any sort of wireless transceivers capable of engaging in wireless, radio frequency (RF) communication. The transceiver(s) 616 can also include other wireless modems, such as a modem for engaging in Wi-Fi, WiMAX, Bluetooth, infrared communication, and the like. The transceiver(s) 616 may include transmitter(s), receiver(s), or both.

First Experimental Example

Out-of-hospital cardiac arrest due to shock-refractory ventricular fibrillation (VF) is associated with relatively poor survival. The ability to predict refractory VF (VF that is permanently terminated only after administering 3 or more shocks) in advance of multiple futile shocks could enable preemptive targeted interventions aimed at improving outcome, such as earlier administration of antiarrhythmics, reconsideration of epinephrine use or dosage, changes in shock delivery strategy, or expedited invasive treatments. This Example utilizes a cohort study of VF out-of-hospital cardiac arrest to develop an ECG-based algorithm to predict patients with refractory VF. Patients with available defibrillator recordings were randomized 80% and 20% into training and test groups, respectively. A random forest classifier applied to 3-second ECG segments immediately before and 1 minute after the initial shock during cardiopulmonary resuscitation was used to predict whether a patient would receive 3 or more shocks during a resuscitation attempt based on singular value decompositions of ECG wavelet transforms. Performance was quantified by area under the receiver operating characteristic curve.

Briefly, of 1376 patients with out-of-hospital cardiac arrest in which VF was the initial rhythm observed by emergency responders, 311 (23%) were female, 864 (63%) experienced refractory VF, and 591 (43%) achieved functional neurological survival. The total number of shocks received by a patient was associated with decreasing likelihood of functional neurological survival, with a relative risk of 0.95 (95% CI, 0.93-0.97) for each additional total number of shocks ($P<0.001$). In the 275 test patients, the area under the receiver operating characteristic curve for predicting refractory VF was 0.85 (95% CI, 0.79-0.89), with specificity of 91%, sensitivity of 63%, and a positive likelihood ratio of 6.7. This Example shows that a machine learning algorithm using ECGs surrounding the initial shock can predict patients likely to experience refractory VF, demonstrating the potential for rescuers to preemptively target interventions in an attempt to improve resuscitation outcome.

Methods

Study Design, Population, and Setting

The experimental example was a retrospective cohort study of patients presenting to EMS with VF-OHCA in a metropolitan EMS system over a 12-year period. Cases were not eligible if the patient was under 18 years of age, had a do-not-resuscitate order, or received a shock by laypersons or police before EMS arrival. Patients were excluded if the defibrillator recording did not contain valid, uninterrupted ECG and transthoracic impedance signals from the time of rhythm analysis before the initial shock through at least the first minute after the initial shock.

The study region is served by a 2-tiered EMS system. First responders are emergency medical technician-firefighters who are equipped with automated external defibrillators, provide basic cardiac life support, and respond to the scene approximately 5 minutes after emergency (9-1-1) dispatch. The second response tier is paramedics who are equipped with manual defibrillators, provide advanced cardiac life support, and arrive on scene an average of 8 minutes after dispatch. EMS follows American Heart Association resuscitation guidelines, which include repeated 2-minute CPR cycles separated by rhythm and pulse checks, as well as pharmacological interventions.

Data Collection and Preprocessing

The study system maintains an OHCA registry that collects demographic, circumstance, care, and outcome information. Patient outcomes include return of spontaneous circulation at the end of EMS care and survival to hospital discharge with functional neurological status as defined by a cerebral performance category score of 1 or 2.

ECG signals were collected from Philips MRx™ and FORERUNNER 3™ (Philips, Bothell, WA), and Physio-Control LIFEPAK 12™ and LIFEPAK 15™ (Stryker, Redmond, WA) defibrillator recordings. ECGs were resampled from native sampling rates of between 125 and 250 Hz to a common frequency of 250 Hz, and filtered from 1 to 40 Hz using a fourth-order Butterworth filter with forward-backward implementation to remove drift and high-frequency noise. Investigators used custom MATLAB™ software (Mathworks, Natick, MA) to identify 2 discrete ECG intervals surrounding the initial shock. Specifically, from each patient, a 3-second ECG segment was collected before the first VF shock during the concurrent CPR pause for defibrillator rhythm analysis, and a 3-second postshock ECG segment 1 minute after the initial shock during the scheduled 2-minute period of CPR (FIG. 3). In the pre-shock segments, the absence of CPR and presence of VF were confirmed by 2-reviewer consensus examination of the ECG and transthoracic impedance signals. By contrast, postshock segments were collected during the scheduled period of CPR (agnostic of the ECG rhythm type or whether chest compressions versus artificial respirations were actively ongoing) to ensure study algorithm consistent with current resuscitation practice.

Outcome

The study outcome was the number of shocks provided by EMS over the course of VF-OHCA treatment. Patients who received ≥3 shocks were defined as shock-refractory (i.e., as having refractory VF), as this shock count corresponds to the guideline threshold for drug initiation (specifically antiarrhythmics). As a sensitivity analysis, we also redefined refractory VF as patients who received greater than 4 shocks.

Algorithm Description

Figure 7:
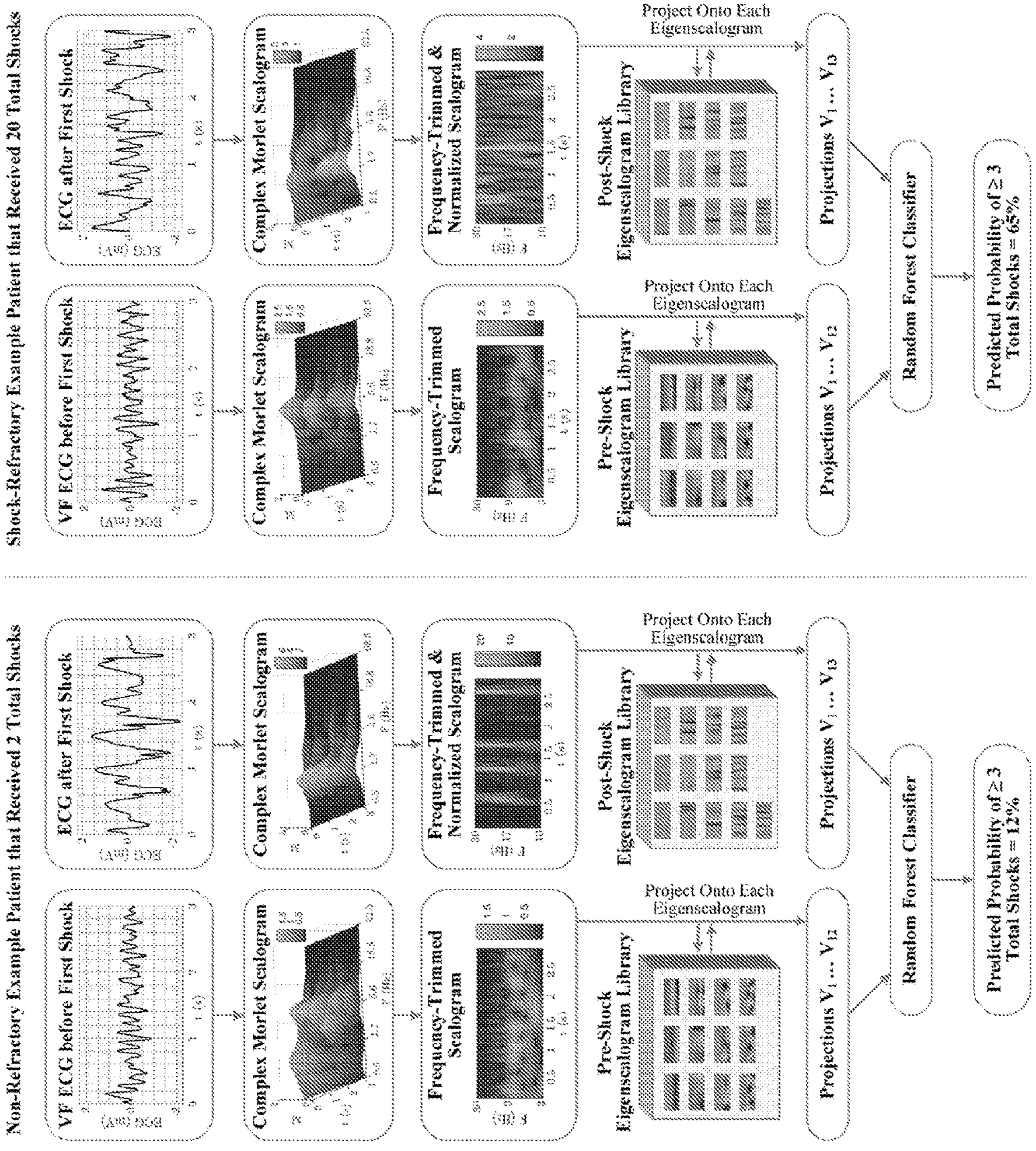
FIG. 7 illustrates a technique applied in a First Experimental Example described below. Examples are shown for a patient requiring 2 shocks (left) vs 20 shocks (right). F indicates frequency; M, magnitude; t, time; and V, projection value.

To predict refractory VF, a given patient's 3-second preshock and postshock ECG segments were first converted into time-frequency representations (scalograms) by convolution with complex Morlet wavelets (see Addison P S. The Illustrated Wavelet Transform Handbook. Taylor & Francis; 2002). In this Example, scalograms were used rather than Fourier transform-based methods because they have properties useful for ECG analysis, such as good temporal resolution at high frequencies and the ability to detect coherent structures in a signal (Addison P S. The Illustrated Wavelet Transform Handbook. Taylor & Francis; 2002; Coult J, et al., Comput Biol Med. 2021; 129:104136; Kwok H, et al., Resuscitation. 2022; 176:90-97). The preshock and postshock scalograms were computed from 2.5 to 30 Hz and 10 to 30 Hz, respectively, to provide a more comprehensive representation of the CPR-free preshock ECG while excluding the majority of CPR artifact (which is concentrated <10 Hz) in the postshock ECG (Gong Y, et al., J Healthc Eng. 2013; 4:185-202). Postshock scalogram values (i.e., wavelet coefficient magnitude envelope values) were normalized within each individual frequency to emphasize underrepresented content, especially high-frequency information above CPR frequencies. Preshock segments were not normalized in order to preserve the absolute magnitude of scalograms generated during VF. Each scalogram was then projected by dot products onto a stored "Eigenscalogram" scalogram library (described in Algorithm Development) to generate a corresponding set of projection (similarity) values. These projection values were used as input features to a machine learning classifier, which predicted the probability of shock-refractory VF (FIG. 7).

Algorithm Development

Patients were randomly divided into 80% training and 20% test groups for algorithm development and evaluation. Scalogram singular modes were generated by transforming the training data set using singular value decomposition, a linear transformation that synthesized the training scalograms into an equal number of singular-mode scalograms sorted by the amount of information (variance) in the data they represented (Sashidhar D, et al., R Soc Open Sci. 2021; 8:210566; Brunton S L, Kutz J N. Data-Driven Science and Engineering: Machine Learning, Dynamical Systems, and Control. 2nd ed. Cambridge University Press; 2022). Because they were ranked by the amount of information they encompassed, a small subset of the leading singular-mode scalograms (i.e. principal components) could be retained to succinctly approximate the unique characteristics of the original training data. We retained the ranked singular-mode scalograms as candidates for potential inclusion in the Eigenscalogram libraries of the algorithm.

A parameter search was performed that varied the number of leading singular modes included in the preshock and postshock Eigenscalogram libraries, the machine learning classifier type, and the classifier parameters. Different classifier types were considered, including random forest, support vector machine, and logistic regression. The parameter search was conducted by cross-validation within training data to select the combination of classifier, classifier parameters, and number of leading modes retained in the Eigenscalogram libraries that yielded the greatest mean area under the receiver operating characteristic curve (AUC) for predicting refractory VF among the cross-validation holdout folds.

The Eigenscalogram libraries yielding the highest mean cross-validation holdout AUC included the first 12 and first 13 singular-mode scalograms generated from the training dataset's preshock and postshock ECG scalograms, respectively. A random forest, a machine learning model that uses an ensemble of decision trees to make majority vote-based predictions, was used as the classifier in this Example. After selecting the Eigenscalogram modes, classifier type, and classifier parameters based on training data cross-validation folds, the entire training dataset was used to generate the final Eigenscalogram libraries and train the final classifier. Odds ratios were used to interpret the univariate association between each of the Eigenscalograms and refractory VF in training data. Some Eigenscalograms were particularly useful to the random forest classifier as measured by relative feature importance, a characteristic confirmed by their univariate association with refractory VF Statistical Methods Patient characteristics were compared according to refractory VF status (<3 shocks versus 3 shocks) and according to inclusion status using Wilcoxon rank-sum tests for continuous variables and $x^2$ tests for proportions. Poisson regression was used to determine the association (relative risk) between increasing shock count and clinical outcome (return of spontaneous circulation and functional neurological survival).

Algorithm classification performance was evaluated in training and test data using AUC. To assess operational implications, classification decision thresholds were selected from training data according to minimum target specificities (80% to 95%), which were applied to determine corresponding sensitivity, specificity, predictive values, and likelihood ratios for the test cohort. The threshold for statistical significance was 0.01. All analyses were performed using MATLAB™.

Results

Study Group and Outcomes

Figure 8:
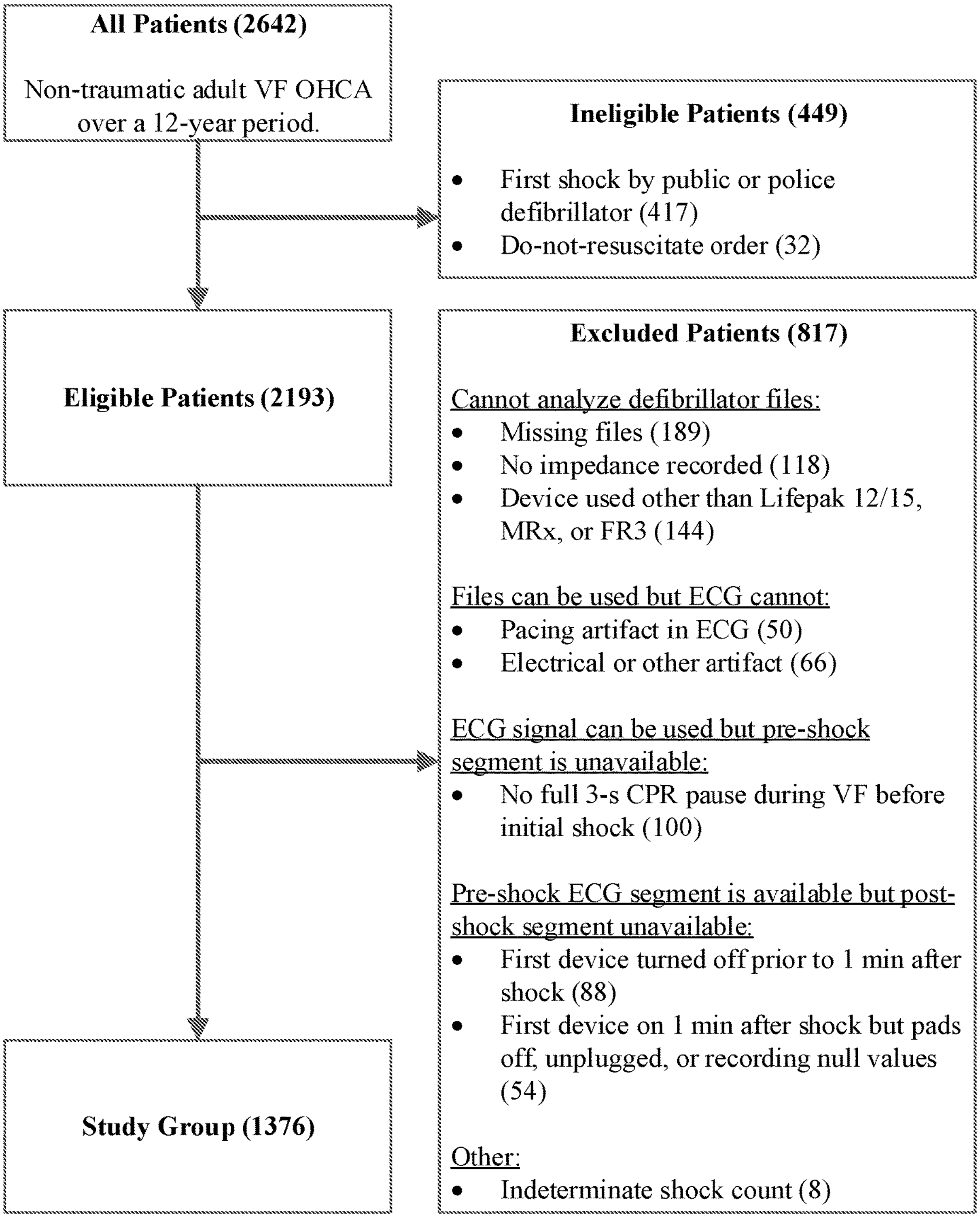
FIG. 8 illustrates the inclusions and exclusions of the study participants analyzed in the Experimental Example.

Table 1 (below) shows study group characteristics. Both refractory and non-refractory patient subsets are described. CPC indicates cerebral performance category; EMS indicates emergency medical services; IQR indicates interquartile range; and ROSC indicates return of spontaneous circulation. Of the 2193 potentially eligible patients who presented to EMS with VF-OHCA between 2008 and 2020, 451 (21%) were excluded due to missing or incompatible defibrillator downloads, and 366 (17%) were excluded due to issues with the defibrillator ECG signal (FIG. 8). Of the resulting 1376 patients in the study group, 311 (23%) were female, 1000 (73%) achieved return of spontaneous circulation at the end of EMS care, and 591 (43%) survived to hospital discharge with functional neurological status (Table 1).

TABLE 1

Study Group Characteristics

| | Study Group | Nonrefractory (<3 total shocks) | Refractory (≥3 total shocks) |
|---|---|---|---|
| Patients, n (%) | 1376 (100) | 512 (37.2) | 864 (62.8) |
| Female, n (%) | 311 (22.6) | 129 (25.2) | 182 (21.1) |
| Age, median (IQR) | 62 (53-72) | 62 (52-73) | 62 (53-72) |
| Cardiac cause, n (%) | 1269 (92.2) | 468 (91.4) | 801 (92.7) |
| Location, n (%) | | | |
| Home | 882 (64.1) | 311 (60.7) | 571 (66.1) |
| Public | 443 (32.2) | 176 (34.4) | 267 (30.9) |
| Nursing Home | 51 (3.7) | 25 (4.9) | 26 (3.) |

TABLE 1-continued

| Study Group Characteristics | | | |
|---|---|---|---|
| | Study Group | Nonrefractory (<3 total shocks) | Refractory (≥3 total shocks) |
| Arrest before EMS arrival, n (%) | 1315 (95.6) | 478 (93.4) | 837 (96.6)* |
| Witnessed arrest, n (%) | 1075 (78.1) | 411 (80.3) | 664 (76.9) |
| Bystander CPR, n (%) | 1042 (79.2+) | 398 (83.3) | 644 (76.9+)* |
| EMS response, min, median (IQR) | 5.2 (4.2-6.6) | 5.2 (4-6.2) | 5.4 (4.3-6.9) |
| Total shocks, median (IQR) | 3 (1-6) | 1 (1-2) | 5 (4-8) |
| ROSC at end of EMS care, n (%) | 1000 (72.7) | 440 (85.9) | 560 (64.8)* |
| Admit to hospital, n (%) | 998 (72.5) | 433 (84.6) | 565 (65.4)* |
| Survive to hospital discharge, n (%) | 633 (46.0) | 299 (58.4) | 334 (38.7)* |
| Survive with CPC 1 or 2, n (%) | 591 (43.0) | 280 (54.7) | 311 (36.0)* |

*P < 0.01 vs nonrefractory patients

+Percentage among patients who arrested before EMS arrival and were thus eligible for bystander cardiopulmonary resuscitation Included versus excluded patients were generally comparable, with similar demographics, circumstances, and survival outcomes, although differences were observed in the proportion of arrests before EMS arrival and in the rate of hospital admissions.

Figure 9:
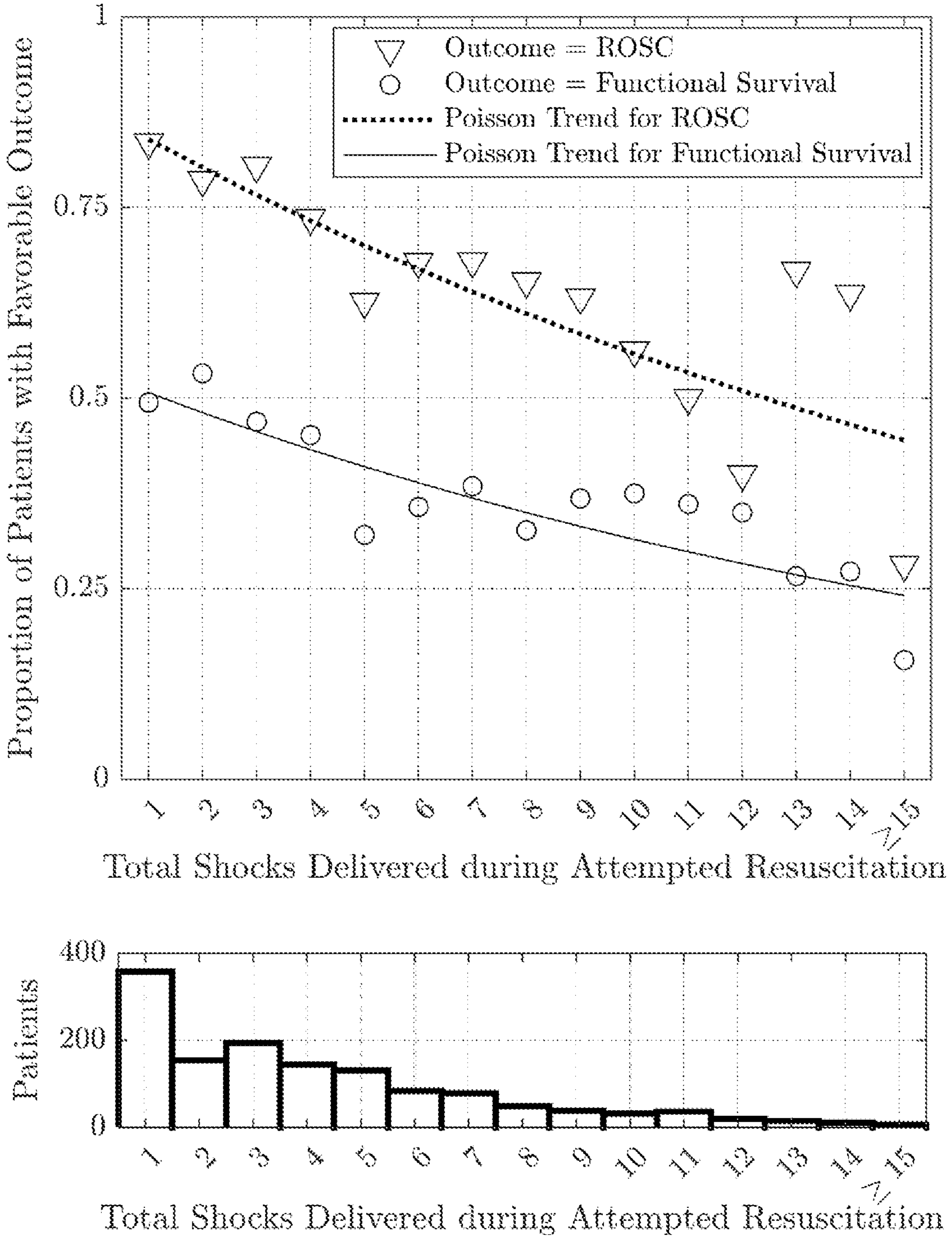
FIG. 9 illustrates unadjusted association of total shocks with patient outcome in the First Experimental Example. The proportion of return of spontaneous circulation (ROSC) and functional survival outcomes versus total shock count are shown with trendlines (top) and the number of patients within each shock count is illustrated (bottom). IQR indicates interquartile range.

The median total number of shocks administered was 3 (interquartile range, 1-6), with 864 (63%) patients having refractory VF as defined by receipt of 3 shocks. Patients with refractory VF were more likely to have arrested before EMS arrival, were less likely to have received bystander CPR, and had worse outcomes (Table 1). When modeling continuous shock count versus outcome, the unadjusted relative risk of good outcome decreased with each successive shock, with a relative risk of return of spontaneous circulation of 0.96 (95% CI, 0.94-0.97; P<0.001) and a relative risk of functional neurological survival of 0.95 (95% CI, 0.93-0.97; P<0.001; FIG. 9).

Algorithm Performance

Figure 10:
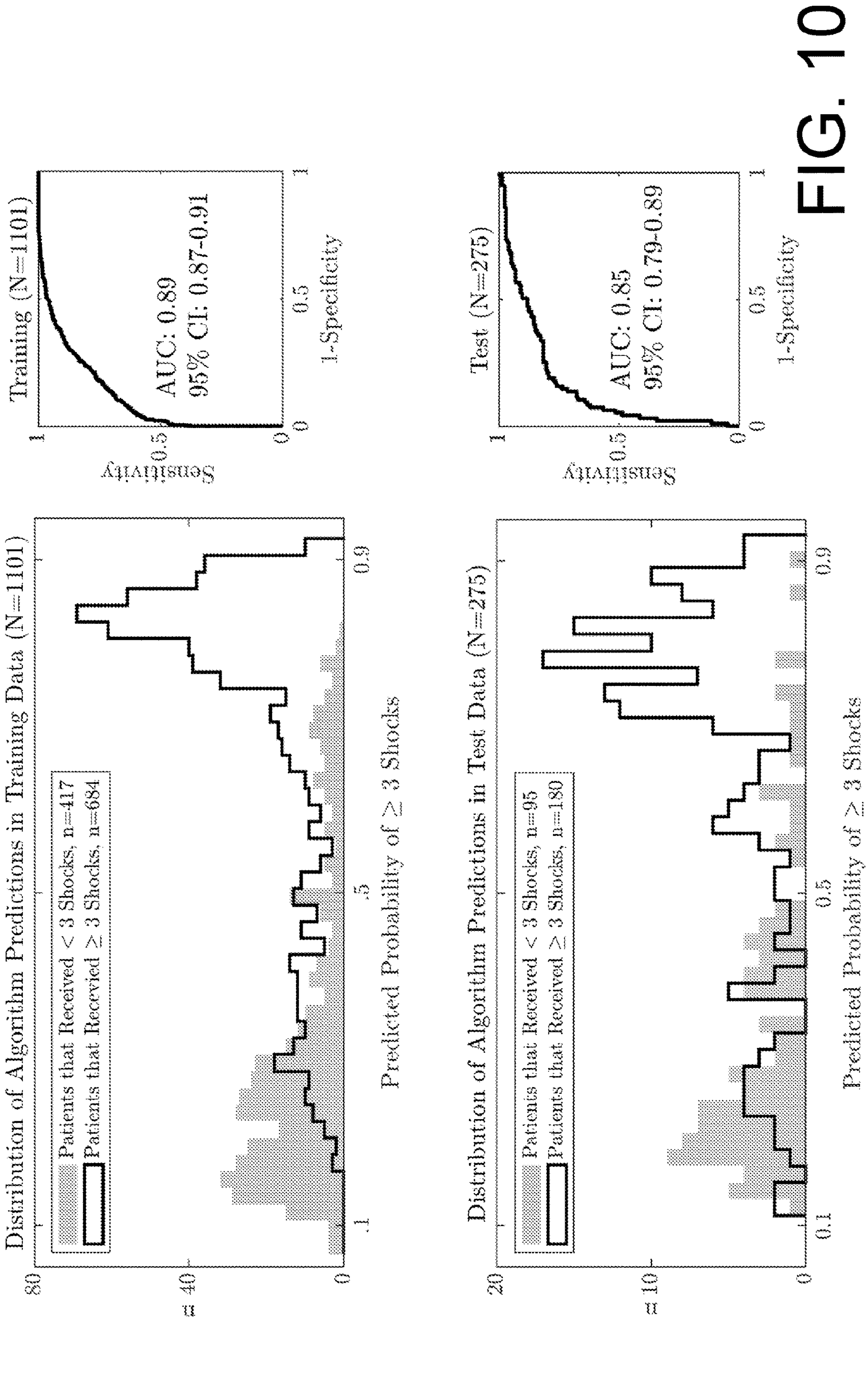
FIG. 10 illustrates training and test results for the model described with respect to the First Experimental Example. Distributions of classifier-predicted probability of refractory VF for training group patients (top, left) and test group patients (bottom, left) patients are shown for each true class. Receiver operating characteristic curves for training (top, right) and test (bottom, right) patients are also illustrated. AUC refers to area under the receiver operating characteristic curve; and N/n to the number of patients.

The AUC values for prediction of shock-refractory patients were 0.89 (95% CI, 0.87-0.91) in the training group (N=1101) and 0.85 (95% CI, 0.79-0.89) in the test group (N=275) (FIG. 10). Table 2 (below) shows sensitivity and specificity values for predicting refractory VF patients (receiving at least 3 shocks) using training (N=1101) and test (N=275). Four classification decision thresholds were selected from training data to achieve each of the four minimum target specificity values and were used to compute the resulting specificity, sensitivity, and likelihood ratio values. Using classification cutoffs derived from the training data, the specificity, sensitivity, predictive values, and likelihood ratios for refractory VF prediction in the test group were determined by observing, for example, a sensitivity of 63%, specificity of 91%, positive predictive value of 93%, and likelihood ratio of 6.7 using the cutoff selected to achieve 90% specificity (Table 2).

TABLE 2

| Method Performance. | | | | |
|---|---|---|---|---|
| Target Specificity | Dataset | Specificity (%) | Sensitivity (%) | Positive predictive value (%) |
| 95% | Training | 95 | 60 | 96 |
| | Test | 93 | 58 | 94 |
| 90% | Training | 90 | 66 | 92 |
| | Test | 91 | 63 | 93 |

TABLE 2-continued

| Method Performance. | | | | |
|---|---|---|---|---|
| Target Specificity | Dataset | Specificity (%) | Sensitivity (%) | Positive predictive value (%) |
| 85% | Training | 85 | 72 | 89 |
| | Test | 84 | 74 | 90 |

Sensitivity Analysis

When refractory VF patients were defined as those whose VF persisted or recurred after 3 shocks and therefore received a total of 4 or more shocks (instead of the guidelines-based definition of 3 or more shocks), the number of patients meeting the definition of refractory VF decreased from 864 (63%) to 670 (49%). The AUC for predicting patients who would receive ≥4 shocks was 0.86 (95% CI, 0.84-0.88) and 0.78 (95% CI, 0.72-0.83) in training and test data, respectively.

Discussion

In this retrospective cohort investigation of VF-OHCA, an ECG-based algorithm predicted refractory VF. Most patients with VF that received ≥3 shocks were correctly identified while maintaining high specificity. These results suggest potential for automated identification of patients at risk of shock-refractory VF within current guidelines for CPR administration during resuscitation. Such insight could be used to better direct early treatment with the goal of reducing total shock count and potentially improving survival.

Refractory VF and Clinical Outcome

It was observed that nearly two-thirds of the cohort of VF OHCA patients had VF that persisted or recurred after 2 shocks and thus received 3 or more total shocks, and about half of the patients had VF that persisted or recurred after 3 shocks and thus received 4 or more total shocks. These observations highlight the common circumstance of refractory VF. Moreover, it was observed that a higher total number of shocks delivered was associated with worse resuscitation outcomes, findings that are supported by previous studies on the negative association of increased shock count with patient outcome (Holmen J, et al., Resuscitation. 2017; 113:33-38; Berdowski J., et al., Circulation. 2010; 122:1101-1108; van Alem A P, et al., Resuscitation. 2003; 59:181-188). Hence, refractory VF occurs commonly in VF-OHCA and is a group that may benefit from preemptive alternative treatment strategies, given the relatively worse prognosis for patients experiencing this condition.

Algorithm Performance Versus Previous Study

A previous investigation proposed a clinical decision rule that relies on cardiac arrest incident variables available to EMS responders (such as such as age, sex, EMS response time, and the patient's initial cardiac rhythm type) to predict refractory VF (i.e. the receipt of 3 total shocks) (Lupton et al., Resuscitation. 2022; 181:60-67). Although this approach is a useful conceptual model, the dependence on clinical and arrest circumstance characteristics, some of which must be observed manually by EMS personnel, may be challenging for automated or time-sensitive operational implementation during resuscitation. In contrast, the ECG-based method of the current study can operate automatically without rescuer input, and its performance (AUC, 0.85) surpasses that of the previous study (AUC, 0.67).

Clinical Implications of Algorithm Performance

The goal of resuscitation treatment is to optimize benefit and minimize risk across what is often a heterogeneous physiological cohort. The study algorithm predicts patients whose VF persists or recurs after until 2 or more EMS shocks current guidelines that recommend CPR throughout the scheduled 2-minute CPR intervals. Given the favorable performance of the algorithm when applied within current clinical guidelines and processing requirements suitable for defibrillator hardware, the proposed method could be integrated into resuscitation practice to better guide treatment. For example, one strategy might use the algorithm to recommend earlier or higher-dose antiarrhythmic treatment or a lower or delayed dose of a vasopressor such as epinephrine (given its potential proarrhythmic effects) for those at high risk of refractory VF (Rahimi M, et al., J Am Heart Assoc. 2022; 11:e023958; Dorian P, et al., N Engl J Med. 2002; 346:884-890; Kudenchuk P J, et al., N Engl J Med. 1999; 341:871-878; Cheskes S, et al., Resuscitation. 2020; 157: 269-271; Lane D J, et al., Heart. 2022; 108:1777-1783; Sousa J, et al., Am J Cardiol. 1992; 69:509-512; Andersen L W, et al., BMJ. 2016; 353:11577; Evans E, et al., BMJ. 2021; 375:e066534). The algorithm might also be used to inform which patients could be considered for modified shock delivery strategies (vector change or double sequential defibrillation) or early transport for advanced hospital care such as an emergent coronary artery intervention or extracorporeal CPR (Cheskes S, et al., N Engl J Med. 2022; 387:1947-1956; Yannopoulos D, et al., Lancet. 2020; 396:1807-1816; Bartos J A, et al., Circulation. 2020; 141:877-886; Maekawa K, et al., Crit Care Med. 2013; 41:1186-1196; Rob D, et al., Crit Care. 2022; 26:330; Belohlavek J, et al., JAMA. 2022; 327:737-747).

Implications of Probability-Based Decision Cutoffs

A decision to modify current guidelines-based treatment may depend on operational cutoffs informed by the performance characteristics of the algorithm (Table 2). For example, a more substantial treatment deviation with higher potential negative side effects might warrant a high level of specificity (and result in lower sensitivity) that would maintain conventional care for most patients whose VF permanently terminates after <3 shocks. Conversely, a change considered to have relatively less risk may permit a lower specificity in order to benefit a greater number of patients with refractory VF.

Artificial Intelligence and Prediction of Refractory VF

The use of artificial intelligence (AI) to automate a more patient-specific approach to resuscitation care using real-time signals such as the ECG is a promising area of investigation (Kwok H, et al., Resuscitation. 2022; 176:90-97; Aiello S R, et al., J Am Heart Assoc. 2021; 10:1-11; Coult J, et al., Resuscitation. 2022; 179:152-162; Chalkias A, et al., Heart Fail Rev. 2019; 24:473-480; Lautz A J, et al., Crit Care Med. 2019; 47:e241-e249). However, clinician adoption of AI to inform medical decisions can be challenged by difficulty in understanding and interpreting the underlying reasoning used by classification algorithms (e.g., deep neural networks) (Chen J H, et al., JAMA. 2022; 328:709709; Brown G, et al., Open Heart. 2022; 9:e001976). This is especially relevant for AI-based methods that might be used to modify clinical guidelines-based care during OHCA resuscitation. In contrast, the proposed machine learning algorithm allows some insight into how refractory VF is predicted by using features that are relatively interpretable in terms of the time-frequency characteristics used to make a classification decision. Examination of preshock ECG characteristics used by the method suggests that initial VF frequency and amplitude may potentially be useful for predicting shock-refractory patients. Likewise, examination of postshock features suggests that after an initial defibrillation attempt, the amount of energy within or the presence of distinctive temporal patterns within higher ECG frequencies (e.g. between 5 to 25 Hz or 10 to 30 Hz) can be used to characterize ECG segments and used to distinguish refractory vs. non-refractory patients. These observations are supported by previous investigations observing that preshock (Coult J, et al., Comput Biol Med. 2021; 129:104136; Coult J, et al., Circ Arrhythm Electrophysiol. 2019; 12:1-10) and postshock (Bhandari S, et al., Resuscitation. 2018; 125:22-27; Coult J, et al., J Electrocardiol. 2018; 51:99-106) ECG characteristics predict patient outcomes. In particular, assessment of the ECG specifically 1 minute after shock is reported to be useful in evaluating the interaction between defibrillation and patient pathophysiology (Gliner B E, White R D., Resuscitation. 1999; 41:133-144). The current study combines these concepts using machine learning to leverage ECG information collected immediately before and 1 minute after initial shock (the latter without requiring CPR interruption) to distinguish patients with refractory VF, supporting the broader advancement toward a greater role of AI in guiding resuscitation care (Brown G, et al., Open Heart. 2022; 9:e001976).

Second Experimental Example

In this Example, shock-refractory VF (i.e., receiving 3 or more total shocks) was predicted during resuscitation without interrupting CPR to allow analysis. While current guidelines protocol for resuscitation requires CPR interruption to allow ECG analysis to determine whether the rhythm is shockable, development of next-generation defibrillator algorithms which detect shockable rhythm during CPR is an active area of investigation. Therefore, a scenario in which rescuers perform uninterrupted CPR until delivering a shock may occur during resuscitation. Prediction of shock-refractory VF in such a scenario would require the refractory VF detection method described in this Example which that can operate regardless of whether CPR is ongoing or paused. A summary of the technique evaluated in this Example is illustrated in FIG. 4.

Figure 11:
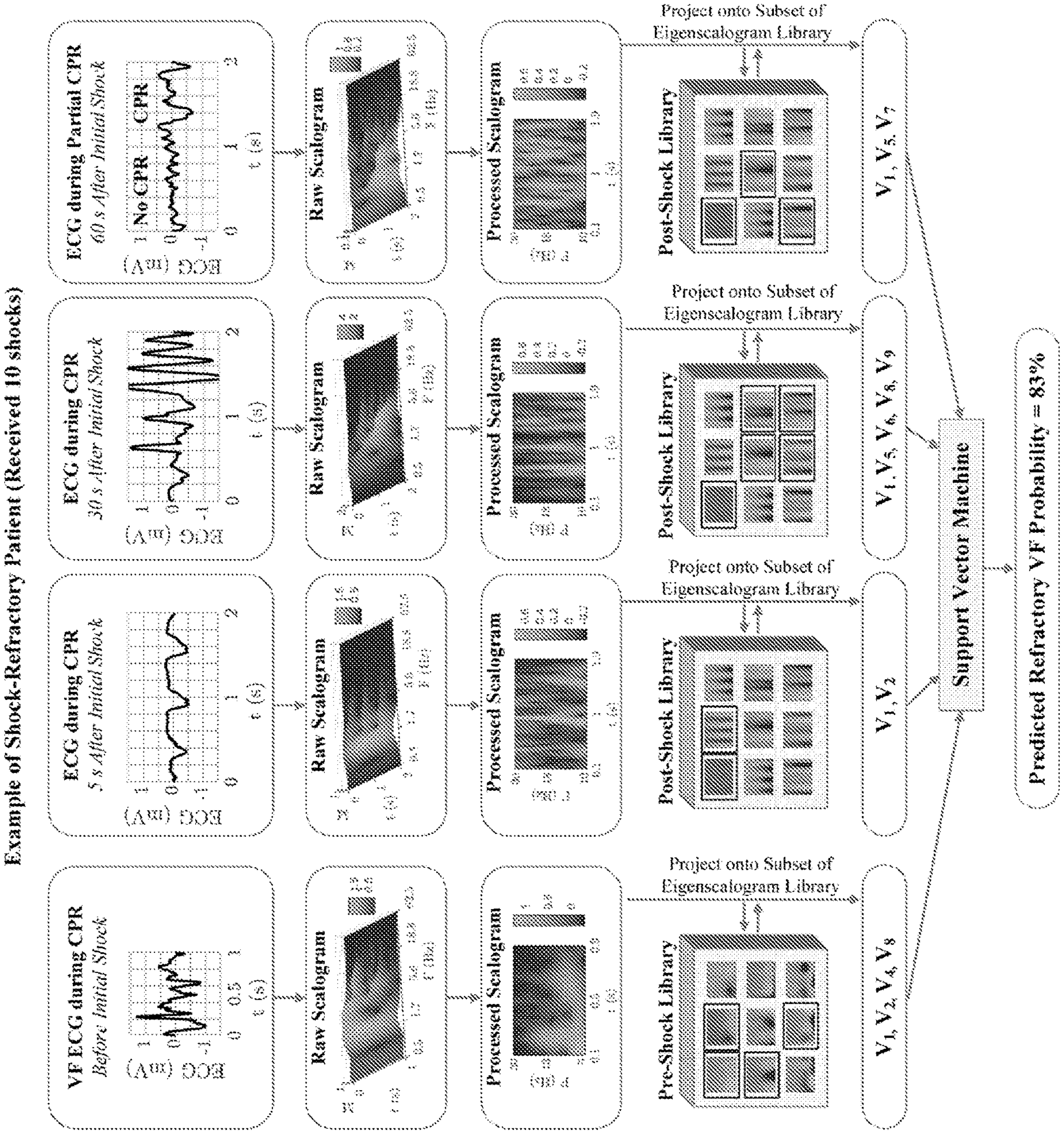
FIG. 11 illustrates a technique applied in a Second Experimental Example described below. An example is shown for a shock-refractory patient that received a total of 10 shocks. Preshock and postschock libraries indicate collections of eigenscalograms. A subset of eigenscalograms is indicated by individual eigenscalogram enclosed in a square outline. F indicates frequency; M, magnitude; t, time; and V, projection value.

In this Example, a retrospective study of adults experiencing out-of-hospital VF cardiac arrests treated by paramedics was performed. This analysis was limited to patients with uninterrupted ECGs available from at least 10 seconds before the initial shock through at least 1 minute following the initial shock. From each patient, ECG segments that would be available during a hypothetical continuous CPR protocol were obtained. Such a hypothetical protocol (illustrated in FIG. 4) may be possible using defibrillators designed to detect shockable rhythms without chest compression interruption, thereby reducing harmful pauses in CPR. During such a hypothetical protocol, the defibrillator would not prompt a CPR pause to allow shock decision analysis, which would incidentally preclude availability of a preshock VF ECG segment for refractory VF prediction. In particular for this Example, a 1-second VF ECG segment during chest compressions prior to shock was obtained from each patient. In addition, three 2-second ECG segments were obtained within the first minute following shock. The three postshock segments were obtained during the scheduled 2-minute CPR periods following initial shock, regardless of the heart rhythm type, the presence of actively ongoing artificial respirations, or the presence of actively ongoing chest compressions. FIG. 11 illustrates how the scalograms are obtained and analyzed in the Second Experimental Example.

In the Second Experimental Example (e.g., with reference to FIG. 11), in contrast to the First Experimental Example (e.g., with reference to FIG. 7), ECG scalograms are compared to a selected subset of eigenscalograms which were selected during algorithm development using patients excluding the current patient. In FIG. 11, the library of available eigenscalograms from which a subset is selected for comparison against an ECG scalogram may be the same library or different than that used for comparison against other ECG scalograms. For example, in FIG. 11, a scalogram from a preshock ECG is compared to a subset of a preshock eigenscalogram library which was generated from patients that exclude the current patient. By contrast, in FIG. 11 each postshock ECG scalogram is compared to a subset of the same postshock eigenscalogram library which was generated from postshock segments of patients excluding the current patient.

Patients in this Example were randomized into 80% training and 20% test groups. In the training group, cross-validation was performed to develop a ML model to predict refractory VF using ECG eigenscalograms. ECG eignscalograms were generated from the training group using singular value decomposition techniques to produce principal components of both normalized and non-normalized ECG scalograms. Subsets of eigenscalograms optimized to predict refractory VF were selected from an analysis of the training group, based on relative feature importance when used as features in an ensemble of decision trees. A test patient's preshock and postshock ECG scalograms are compared to subsets of eigenscalograms using dot products, and the similarity values used as features for a ML model (e.g. support vector machine). Performance of the final algorithm was assessed by AUC. Classification decision thresholds for sensitivity and specificity calculation were selected in training data to achieve 90% specificity.

Table 3 illustrates the performance of the technique in the Second Experimental Example for predicting refractory VF, as compared to the technique described above with respect to the First Experimental Example. Of 1,024 included patients, 642 (63%) had refractory VF, 222 (22%) were female, median age was 62, median shocks was 3 (IQR: 1-6), median EMS response was 5 min (IQR: 4-7), 813 (79%) were witnessed, 713 (70%) received bystander CPR, and 464 (45%) survived to discharge. Non-refractory vs. refractory VF patient survival was 58% vs. 38% ($p<0.001$ for difference). CI indicates confidence interval and N indicates number of patients.

TABLE 3

Technique Performance.

| Technique | Dataset (N) | Specificity (%) | Sensitivity (%) | AUC (95% CI) |
|---|---|---|---|---|
| Second Experimental Example | Training (820) | 90 | 59 | 0.83 (0.80-0.86) |
| | Test (204) | 89 | 60 | 0.83 (0.76-0.88) |
| First Experimental Example | Training (1101) | 90 | 66 | 0.89 (0.87-0.91) |
| | Test (275) | 90 | 63 | 0.85 (0.79-0.89) |

This study validates a ML-based technique using four ECG segments surrounding the initial shock to predict patients likely to experience refractory VF without requiring CPR pause to allow ECG analysis. The method has only slightly reduced performance (test group AUC difference of 0.02) compared to the technique described in the First Experimental Example. The results suggest potential for preemptive interventions targeted to mitigate refractory VF and improve patient outcomes within the context of next-generation defibrillators that do not require CPR pause for ECG analysis.

EXAMPLE CLAUSES

1. A medical device, including: at least one sensor configured to detect an electrocardiogram (ECG) of a patient who is in a state of cardiac arrest; an output device configured to output an instruction to administer a treatment; and a processor configured to: identify a pre-shock segment of the ECG, the pre-shock segment being detected by the sensor when a heart of the patient is in a state of ventricular fibrillation (VF) during a time interval preceding administration of an initial electrical shock to the heart of the patient; identify at least one post-shock segment of the ECG, the at least one post-shock segment being detected by the sensor during a time interval following administration of the initial electrical shock to the heart of the patient; predict, based on the pre-shock segment and the at least one post-shock segment, that the patient is exhibiting shock-refractory VF by: converting the pre-shock segment into a first scalogram; converting the at least one post-shock segment into at least one second scalogram; generating comparisons between the first scalogram and the at least one second scalogram to eigenscalograms; and determining whether the comparisons are indicative of shock-refractory VF; and in response to predicting that the patient is exhibiting shock-refractory VF, cause the output device to output the instruction to administer a treatment.
2. The medical device of clause 1, wherein the time interval proceeding administration of the initial electrical shock to the heart of the patient ends within one minute after administration of the initial electrical shock.
3. The medical device of clause 1 or 2, wherein the processor is configured to convert the pre-shock segment into the first scalogram by performing a wavelet transform on the pre-shock segment, and wherein the processor is configured to convert the at least one post-shock segment into the at least one second scalogram by performing the wavelet transform on the at least one post-shock segment.
4. The medical device of clause 3, wherein the wavelet transform includes a Morlet wavelet transform.

5. The medical device of any of clauses 1 to 4, wherein the patient is receiving first chest compressions during the time interval preceding administration of the initial electrical shock to the heart of the patient, and/or wherein the patient is receiving second chest compressions during the time interval following the administration of the initial electrical shock to the heart of the patient.
6. The medical device of clause 5, wherein the processor is further configured to remove artifacts associated with the first chest compressions from the pre-shock segment of the ECG, and/or wherein the processor is further configured to reduce artifacts associated with the second chest compressions from the at least one post-shock segment of the ECG.
7. The medical device of clause 6, wherein the processor is further configured to: reduce artifacts associated with the second chest compressions from the at least one post-shock segment of the ECG by normalizing wavelet coefficient magnitude values of the at least one second scalogram.
8. The medical device of clause 7, wherein the processor is further configured to: normalize the first scalograms and the second scalograms by dividing wavelet coefficient magnitude values within each scalogram frequency by at least one of a maximum, median, or mean wavelet coefficient magnitude within each scalogram frequency.
9. The medical device of any of clauses 1 to 8, wherein the treatment includes administration of an antiarrhythmic medication to the patient, administration of a subsequent electrical shock at a different vector than the initial electrical shock, administration of a double-sequential defibrillation (DSD) treatment, administration of cardiac catheterization treatment, withholding of vasopressor treatment, or administration of extracorporeal membrane oxygenation treatment.
10. The medical device of any of clauses 1 to 9, wherein the shock-refractory VF indicates that the VF of the patient persists when at least two total shocks have been administered to the heart of the patient.
11. The medical device of any of clauses 1 to 10, wherein generating comparisons between the first scalogram and the at least one second scalogram to eigenscalograms includes: identifying pre-shock dot products by comparing the pre-shock scalogram to the eigenscalograms; identifying post-shock dot products by comparing the at least one post-shock scalogram to the eigenscalograms, and wherein determining that the comparisons are indicative of shock-refractory VF includes inputting the pre-shock dot products and the post-shock dot products into a trained machine learning (ML) model; and receiving a classification that the patient is susceptible to shock-refractory VF from the trained ML model.
12. The medical device of clause 11, wherein the processor is further configured to: trim the first scalogram to a first frequency range; and/or trim the at least one post-shock scalogram to a second frequency range.
13. The medical device of clause 12, wherein the first frequency range is between about 5 Hz to about 30 Hz, and wherein the second frequency range is between about 10 Hz and 30 Hz.
14. The medical device of any of clauses 11 to 13, wherein the trained ML model includes at least one of a random forest model, a support vector machine (SVM), or a k-nearest neighbor model.
15. The medical device of any of clauses 11 to 14, wherein receiving the classification that the patient is susceptible to shock-refractory VF from the trained ML model includes: receiving, from the trained ML model, a probability that the patient is susceptible to shock-refractory VF; and determining that the probability exceeds a predetermined probability threshold.
16. The medical device of any of clauses 1 to 15, wherein the at least one post-shock segment includes multiple post-shock segments.
17. The medical device of clause 16, wherein the multiple post-shock segments include a first post-shock segment beginning at between about 1 second to about 20 seconds following shock, a second post-shock segment beginning at about 20 seconds to about 40 seconds following shock, and a third post-shock segment beginning at about 40 seconds to about 60 seconds following shock.
18. The medical device of any of clauses 1 to 17, wherein the output device is configured to output the instruction to administer the treatment prior to administration of a subsequent electrical shock to the patient.
19. The medical device of any of clauses 1 to 18, wherein the output device is configured to output the instruction to administer the treatment during a CPR period proceeding the administration of the initial electrical shock to the patient.
20. The medical device of clause 19, wherein the CPR period ends about 2 minutes after administration of the initial electrical shock to the patient.
21. A method, including: identifying a first segment of an electrocardiogram (ECG) that ends prior to administration of an electrical shock; identifying at least one second segment of the ECG that begins after the administration of the electrical shock; predicting, based on the first segment and the at least one second segment, that the ECG is indicative of a defibrillation-resistant heart rhythm by: converting the first segment into a first scalogram; comparing the first scalogram to eigenscalograms; converting the at least one second segment into at least one second scalogram; and comparing the at least one second scalogram to eigenscalograms; and outputting an indication of the predicted defibrillation-resistant heart rhythm.
22. The method of clause 21, wherein converting the first segment into a first scalogram includes performing a wavelet transform on the first segment.
23. The method of clause 21 or 22, wherein converting the at least one second segment into at least one second scalogram includes performing a wavelet transform on the at least one second segment.
24. The method of any of clauses 21 to 23, wherein the first segment includes chest compression artifacts.
25. The method of clause 24, wherein the method further includes reducing the chest compression artifacts from the first segment.
26. The method of any of clauses 21 to 25, wherein the at least one second segment includes chest compression artifacts.
27. The method of clause 26, further including: reducing the chest compression artifacts from the at least one second segment.
28. The method of clause 26 or 27, wherein reducing the artifacts associated with the second segment chest compressions includes normalizing wavelet coefficient magnitude values of the second scalograms.

29. The method of clause 28, wherein normalizing the wavelet coefficient magnitude values of the second scalograms includes dividing the wavelet coefficient magnitude values within each scalogram frequency by at least one of a maximum, a median, or a mean wavelet coefficient magnitude within each scalogram frequency.
30. The method of any of clauses 21 to 29, wherein the electrical shock is an initial electrical shock administered to a subject during a rescue event.
31. The method of any of clauses 21 to 30, wherein the electrical shock is administered to a heart, and wherein the ECG is indicative of an electrical signal output by the heart.
32. The method of any of clauses 21 to 31, wherein the electrical shock is a biphasic shock having an energy in a range of about 100 Joules (J) to about 360 J.
33. The method of any of clauses 21 to 32, further including: trimming the first scalogram to a first frequency range, and/or trimming the second scalogram to a second frequency range.
34. The method of clause 33, wherein the first frequency range is about 2 Hz to about 35 Hz or about 5 Hz to 30 Hz, and/or wherein the second frequency range is about 5 Hz to about 35 Hz.
35. The method of clause 33 or 34, wherein the first frequency range is broader than the second frequency range.
36. The method of any of clauses 21 to 35, wherein comparing the first scalogram to eigenscalograms includes determining first dot products of the first segment, and/or wherein comparing the at least one second scalogram to the eigenscalograms includes determining second dot products of the at least one second segment.
37. The method of clause 36, wherein determining that the ECG is indicative of the defibrillation-resistant heart rhythm includes inputting the first dot products and the second dot products into a classifier.
38. The method of clause 37, wherein the classifier includes at least one of a trained random forest model, SVM, or k-nearest neighbor model.
39. The method of clause 37 or 38, wherein determining that the ECG is indicative of the defibrillation-resistant heart rhythm includes: receiving, from the classifier, a probability that the ECG is indicative of the defibrillation-resistant heart rhythm; and determining that the probability exceeds a threshold probability.
40. The method of any of clauses 21 to 39, wherein the defibrillation-resistant heart rhythm includes shock-refractory VF.
41. The method of any of clauses 21 to 40, wherein the ECG is indicative of the defibrillation-resistant heart rhythm by exhibiting VF that will be present after at least two electrical shocks are administered to a subject unless the subject receives an additional treatment.
42. The method of any of clauses 21 to 41, further including: outputting an instruction to administer an additional treatment.
43. The method of clause 42, the electrical shock being a first electrical shock, wherein the additional treatment includes at least one of administration of an antiarrhythmic medication, administration of a second electrical shock at a different vector than the first electric shock, administration of the second electrical shock at a higher energy level than the first electrical shock, administration of extracorporeal membrane oxygenation, administration of a cardiac catheterization treatment, or administration of DSD.
44. The method of clause 42 or 43, further including: administering an additional treatment.
45. The method of any of clauses 21 to 44, wherein predicting, based on the first segment and the second segment, that the ECG is indicative of the defibrillation-resistant heart rhythm further includes: determining that the first segment exhibits VF; and determining that at least one of a frequency, energy, or magnitude of the VF is below a threshold.
46. The method of any of clauses 21 to 45, wherein predicting, based on the first segment and the at least one second segment, that the ECG is indicative of the defibrillation-resistant heart rhythm further includes: determining that an energy of the at least one second segment is below a threshold.
47. The method of any of clauses 21 to 46, wherein predicting, based on the first segment and the at least one second segment, that the ECG is indicative of the defibrillation-resistant heart rhythm further includes: determining that the at least one second segment exhibits VF, ventricular asystole, or QRS complexes, the QRS complexes each having greater than a threshold QRS width and/or lower than a threshold R-to-R interval.
48. The method of any of clauses 21 to 47, wherein outputting the indication of the predicted defibrillation-resistant heart rhythm includes outputting a visual alert on a display, outputting an audible alert using a speaker, or transmitting a signal to an external computing device.
49. The method of any of clauses 21 to 48, wherein outputting the indication of the predicted defibrillation-resistant heart rhythm occurs during a CPR period following the electrical shock.
50. The method of any of clauses 21 to 49, wherein outputting the indication of the predicted defibrillation-resistant heart rhythm occurs within two minutes of administration of the electrical shock.
51. The method of any of clauses 21 to 50, the electric shock being a first electric shock, wherein outputting the indication of the predicted defibrillation-resistant heart rhythm includes outputting a recommendation to administer an antiarrhythmic medication, to administer a second electrical shock at a different vector than the first electric shock, to administer the second electrical shock at a higher energy level than the first electrical shock, to administer extracorporeal life support, to administer cardiac catheterization treatment, to administer a DSD treatment, or to perform an additional diagnostic test.
52. The method of any of clauses 21 to 51, wherein identifying the at least one second segment of the ECG that begins after the administration of the electrical shock includes: identifying a third segment of the ECG that begins after the administration of the electrical shock; determining that the defibrillation-resistant heart rhythm cannot be predicted based on the first segment and the third segment; and in response to determining that the defibrillation-resistant heart rhythm cannot be predicted based on the first segment and the third segment, identifying the at least one second segment of the ECG that includes the third segment and a fourth segment of the ECG that begins after the third segment.

53. The method of any of clauses 21 to 51, wherein the at least one second segment of the ECG includes multiple segments of the ECG that begin after the administration of the electrical shock.
54. The method of clause 53, wherein the multiple segments include at least three segments.
55. The method of clause 53 or 54, wherein the multiple segments have lengths in a range of about 1 second to about 20 seconds.
56. The method of any of clauses 53 to 55, wherein the multiple segments occur within about 1 minute after the administration of the electrical shock.
57. A method of treating refractory ventricular fibrillation in a subject in need thereof, the method including: identifying a first segment of an electrocardiogram (ECG) that ends prior to administration of an electrical shock; identifying a second segment of the ECG that begins after the administration of the electrical shock; predicting, based on the first segment and the second segment, that the subject has a defibrillation-resistant heart rhythm; outputting an indication of the predicted defibrillation-resistant heart rhythm; and administering an antiarrhythmic medication.
58. A computing device, including: at least one processor; and memory storing instructions that, when executed by the at least one processor, cause the at least one processor to perform operations including: the method of any of clauses 21 to 57.
59. A defibrillator including: a processor configured to perform the method of any of clauses 21 to 57; a first circuit configured to detect the ECG; and a second circuit configured to administer the electrical shock.
60. The defibrillator of clause 59, further including: an output device configured to present the indication of the predicted defibrillation-resistant heart rhythm.
61. A non-transitory computer-readable medium encoding instructions for performing the method of any of clauses 21 to 57.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

The present disclosure cites to various documents, articles, books, printed publications, and other references. Each of these references is hereby incorporated by reference in its entirety.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements or in rounding the value to a specific number of significant digits.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

What is claimed is:

1. A medical device, comprising:

at least one sensor configured to detect an electrocardiogram (ECG) of a patient who is in a state of cardiac arrest;

an output device configured to output an instruction to administer a treatment; and a processor configured to:

identify a pre-shock segment of the ECG, the pre-shock segment being detected by the sensor when a heart of the patient is in a state of ventricular fibrillation (VF) during a time interval preceding administration of an initial electrical shock to the heart of the patient;

identify at least one post-shock segment of the ECG, the at least one post-shock segment being detected by the sensor during a time interval following administration of the initial electrical shock to the heart of the patient;

predict, based on the pre-shock segment and the at least one post-shock segment, that the patient is exhibiting shock-refractory VF by:

converting the pre-shock segment into a first scalogram;

converting the at least one post-shock segment into at least one second scalogram;

generating comparisons between the first scalogram and the at least one second scalogram to eigenscalograms; and determining whether the comparisons are indicative of shock-refractory VF; and in response to predicting that the patient is exhibiting shock-refractory VF, cause the output device to output the instruction to administer a treatment.

2. The medical device of claim 1, wherein the processor is configured to convert the pre-shock segment into the first scalogram by performing a Morlet wavelet transform on the pre-shock segment, and wherein the processor is configured to convert the at least one post-shock segment into the at least one second scalogram by performing the Morlet wavelet transform on the at least one post-shock segment.

3. The medical device of claim 1, wherein the patient is receiving first chest compressions during the time interval preceding administration of the initial electrical shock to the heart of the patient and the processor is further configured to remove artifacts associated with the first chest compressions from the pre-shock segment of the ECG, and/or wherein the patient is receiving second chest compressions during the time interval following the administration of the initial electrical shock to the heart of the patient and the processor is further configured to reduce artifacts associated with the second chest compressions from the at least one post-shock segment of the ECG.

4. The medical device of claim 3, wherein the processor is further configured to:

reduce artifacts associated with the second chest compressions from the at least one post-shock segment of the ECG by normalizing wavelet coefficient magnitude values of the at least one second scalogram, and normalize the first scalograms and the second scalograms by dividing wavelet coefficient magnitude values within each scalogram frequency by at least one of a maximum, median, or mean wavelet coefficient magnitude within each scalogram frequency.

5. The medical device of claim 1, wherein the treatment comprises administration of an antiarrhythmic medication to the patient, administration of a subsequent electrical shock at a different vector than the initial electrical shock, administration of a double-sequential defibrillation (DSD) treatment, administration of cardiac catheterization treatment, withholding of vasopressor treatment, or administration of extracorporeal membrane oxygenation treatment.

6. The medical device of claim 1, wherein generating comparisons between the first scalogram and the at least one second scalogram to eigenscalograms comprises:

identifying pre-shock dot products by comparing the pre-shock scalogram to the eigenscalograms;

identifying post-shock dot products by comparing the at least one post-shock scalogram to the eigenscalograms, and wherein determining that the comparisons are indicative of shock-refractory VF comprises inputting the pre-shock dot products and the post-shock dot products into a trained machine learning (ML) model; and receiving a classification that the patient is susceptible to shock-refractory VF from the trained ML model.

7. The medical device of claim 1, wherein the output device is configured to output the instruction to administer the treatment during a CPR period following the administration of the initial electrical shock to the patient, and wherein the CPR period ends about 2 minutes after administration of the initial electrical shock to the patient.

8. A method, comprising:

identifying a first segment of an electrocardiogram (ECG) that ends prior to administration of an electrical shock;

identifying at least one second segment of the ECG that begins after the administration of the electrical shock;

predicting, based on the first segment and the at least one second segment, that the ECG is indicative of a defibrillation-resistant heart rhythm by:

converting the first segment into a first scalogram;

comparing the first scalogram to eigenscalograms;

converting the at least one second segment into at least one second scalogram; and comparing the at least one second scalogram to eigenscalograms; and outputting an indication of the predicted defibrillation-resistant heart rhythm.

9. The method of claim 8, wherein converting the first segment into a first scalogram comprises performing a wavelet transform on the first segment, and wherein converting the at least one second segment into at least one second scalogram comprises performing a wavelet transform on the at least one second segment.

10. The method of claim 8, wherein the at least one second segment comprises chest compression artifacts, and wherein the method further comprises:

reducing the chest compression artifacts from the at least one segment by normalizing wavelet coefficient magnitude values of the second scalograms.

11. The method of claim 10, wherein normalizing the wavelet coefficient magnitude values of the second scalograms comprises dividing the wavelet coefficient magnitude values within each scalogram frequency by at least one of a maximum, a median, or a mean wavelet coefficient magnitude within each scalogram frequency.

12. The method of claim 8, further comprising:

trimming the first scalogram to a first frequency range, trimming the second scalogram to a second frequency range, and wherein the first frequency range is broader than the second frequency range.

13. The method of claim 8, wherein comparing the first scalogram to eigenscalograms comprises determining first dot products of the first segment, wherein comparing the at least one second scalogram to the eigenscalograms comprises determining second dot products of the at least one second segment, and wherein determining that the ECG is indicative of the defibrillation-resistant heart rhythm comprises inputting the first dot products and the second dot products into a classifier, the classifier being at least one of a trained random forest model, SVM, or k-nearest neighbor model.

14. The method of claim 8, the electrical shock being a first electrical shock, the method further comprising:

outputting an instruction to administer an additional treatment, wherein the additional treatment comprises at least one of administration of an antiarrhythmic medication, administration of a second electrical shock at a different vector than the first electric shock, administration of the second electrical shock at a higher energy level than the first electrical shock, administration of extracorporeal membrane oxygenation, administration of a cardiac catheterization treatment, or administration of DSD.

15. The method of claim 8, wherein predicting, based on the first segment and the second segment, that the ECG is indicative of the defibrillation-resistant heart rhythm further comprises:

determining that the first segment exhibits VF; and determining that at least one of a frequency, energy, or magnitude of the VF is below a threshold.

16. The method of claim 8, wherein outputting the indication of the predicted defibrillation-resistant heart rhythm occurs during a CPR period following the electrical shock, and/or wherein outputting the indication of the predicted defibrillation-resistant heart rhythm occurs within two minutes of administration of the electrical shock.

17. The method of claim 8, wherein identifying the at least one second segment of the ECG that begins after the administration of the electrical shock comprises:

identifying a third segment of the ECG that begins after the administration of the electrical shock;

determining that the defibrillation-resistant heart rhythm cannot be predicted based on the first segment and the third segment; and in response to determining that the defibrillation-resistant heart rhythm cannot be predicted based on the first segment and the third segment, identifying the at least one second segment of the ECG that comprises the third segment and a fourth segment of the ECG that begins after the third segment.

18. The method of claim 8, wherein the at least one second segment of the ECG comprises multiple segments of the ECG that begin after the administration of the electrical shock, and wherein the multiple segments occur within about 1 minute after the administration of the electrical shock.

19. A computing device, comprising:

at least one processor; and memory storing instructions that, when executed by the at least one processor, cause the at least one processor to perform operations comprising:

identifying a first segment of an electrocardiogram (ECG) that ends prior to administration of an electrical shock;

identifying at least one second segment of the ECG that begins after the administration of the electrical shock;

predicting, based on the first segment and the at least one second segment, that the ECG is indicative of a defibrillation-resistant heart rhythm by:

converting the first segment into a first scalogram;

comparing the first scalogram to eigenscalograms:

converting the at least one second segment into at least one second scalogram; and comparing the at least one second scalogram to eigenscalograms; and outputting an indication of the predicted defibrillation-resistant heart rhythm.

20. The computing device of claim 19, wherein the operations further comprise:

trimming the first scalogram to a first frequency range, trimming the second scalogram to a second frequency range, and wherein the first frequency range is broader than the second frequency range.

* * * * *